United States Patent

Maggio

[11] Patent Number: 5,986,136
[45] Date of Patent: Nov. 16, 1999

[54] PHOTOLABELING REAGENT

[75] Inventor: John E. Maggio, Cinncinati, Ohio

[73] Assignee: President and Fellows of Harvard College, Cambridge, Mass.

[21] Appl. No.: 09/057,799

[22] Filed: Apr. 9, 1998

Related U.S. Application Data

[60] Provisional application No. 60/043,019, Apr. 15, 1997.

[51] Int. Cl.⁶ .................................................. C07C 49/786
[52] U.S. Cl. ........................... 564/328; 568/332; 522/46; 524/359; 562/445; 564/329; 514/2
[58] Field of Search ..................................... 564/328, 329; 568/332; 522/46; 524/359; 562/445

[56] References Cited

U.S. PATENT DOCUMENTS

| | | | |
|---|---|---|---|
| 4,442,090 | 4/1984 | Kakeya | 424/178 |
| 4,757,066 | 7/1988 | Shiokari | 514/210 |
| 4,762,881 | 8/1988 | Kauer et al. | 525/54.11 |
| 5,266,565 | 11/1993 | Lacoste | 514/114 |

FOREIGN PATENT DOCUMENTS

94/06761   3/1994   WIPO .

OTHER PUBLICATIONS

Tripp, J Med Chem 16, 60–64, 1973.
Wilson, Biochem 36, 4542, 1997.
Chem. Abstr. 47, 1639e, 1953.

*Primary Examiner*—Michael P. Woodward
*Assistant Examiner*—David Lukton
*Attorney, Agent, or Firm*—Hamilton, Brook, Smith & Reynolds, PC

[57] ABSTRACT

Disclosed is a compound represent by the following structural formula:

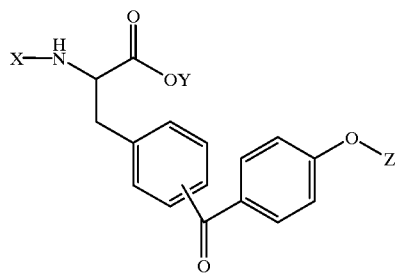

X is —H or an amine protecting group; —OY is —OH, an activating group for a carboxylic acid or a protecting group for a carboxylic acid; Z is —H or a phenolic protecting group, with the proviso that Z is not a straight chained, unsaturated alkyl group such as, for example, methyl or ethyl, and at least one of X, Y or Z is not —H.

Also disclosed is a photoreactive polypeptide having a polypeptide chain comprising a residue of the compound described above. Also disclosed is a method of labeling a target molecule which forms a complex with the photoreactive polypolypeptide by photolyzing the photoreactive polypeptide when complexed with the target molecule.

21 Claims, 6 Drawing Sheets

PHOTOLABELING REAGENT

RELATED APPLICATIONS

This application claims the benefit of priority to U.S. Provisional Application Ser. No. 60/043,019, filed on Apr. 15, 1997, the entire teachings of which are incorporated herein by reference.

GOVERNMENT FUNDING

This invention was made with support from the U.S. government with funding under NIH Grant No. GM15904. The government has certain rights in the invention.

BACKGROUND OF THE INVENTION

Photoaffinity labeling has been an important method for the direct elucidation of intermolecular interactions in biological systems (Bayley, H., *Photogenerated Reagents in Biochemistry and Molecular Biology*, Elsevier, Amsterdam (1983)) since its introduction by Westheimer and coworkers (Singh, A., Thornton, E. R. and Westheimer, F. H., *J. Biol. Chem.* 237, 3006–3008 (1962)) more than three decades ago. A variety of photophores have been employed, most relying on photoconversion of diazo compounds, azides, or diazirines to nitrenes or carbenes (Bayley, H., *Photogenerated Reagents in Biochemistry and Molecular Biology* (1983), Elsevier, Amsterdam. These reactive intermediates have the disadvantage of reacting rapidly with water, leading to very low photoinsertion yields in most cases. The introduction of benzophenones as photoactivatable reagents by Galardy, R. E., Craig, L. C. and Printz, N. P., *Nature New Biol.* 242, 127–128 (1973) led to the recognition of a significant advantage of this photophore over the nitrene and carbene precursors: the excited state of the benzophenones, a triplet biradical, is essentially inert toward water. Other advantages of this photophore over previous ones include stability to ambient light, activation at longer wavelengths (thus minimizing photolytic damage to proteins), and a much wider range of chemical stability. The photochemistry of benzophenones has been reviewed (Dorman, G., and Prestwich, G. D., *Biochemistry* 33, 5661–5673 (1994)). Introduction of the amino acid 4-benzoylphenylalanine (BPA[1]) by Kauer, J. C., Erickson-Vitanen, S. Wolfe, H. R. J. and DeGrado, W. F., *J. Biol. Chem.* 261:10695–10400 (1986) allowed direct incorporation of a benzophenone photophore at a defined position into peptides by solid-phase synthesis, bringing a significant advance in the application of photoaffinity labeling to the study of peptide-protein interactions (Adams, A. E., Pines, M., Nakamoto, C., Behar, V., Yang, Q. M., Bessalle, R., Chorev, M., Rosenblatt, M., Levine, M. A. and Suva, L. J., *Biochemistry* 34, 10553–105539 (1995); Behar, V., Pines, M., Nakamoto, C., Greenberg, Z., Bisello, A., Stueckle, S. M., Bessalle, R., Usdin, T. B., Chorev, M., Rosenblatt, M. and Suva., L. J., *Endocrinology* 137, 2748–2757 (1996); Blanton, M. P., Li, Y. M., Stimson, E. R., Maggio, J. E. and Cohen, J. B., *Mol. Pharmacol.* 46, 1048–1055 (1994); Bosse, R., Servant, G., Zhou, L.-M., Guillemette, G. and Escher, E., *Regul. Peptides* 44, 215–223 (1993); Boyd, N. D., Macdonald, S. G., Kage, R., Luber-Narod, J. and Leeman, S. E., *Ann. New York Acad. Sci.* 632, 79–93 (1991a); Boyd, N. D., White C. F., Cerpa, R, Kaiser, E. T. and Leeman, S. E., *Biochemistry* 30, 336–342 (1991b); Boyd, N. D., Kage, R. K. and Leeman, S. E., The *Tachykinin Receptors* (Buck, S. H., ed) pp. 219–236, Humana Press, Totowa, N.J. (1994); Boyd, N. D., Kage, R. K., Dumas, J. J., Krause, J. E. and Leeman, S. E., *Proc. Natl. Acad. Sci. USA* 93, 433–437 (1996); Gao, Z.-H, Zhi, G., Herring, B. P., Moomaw, Deogny, L., Slaughter, C. A. and Stull, J. T., *J. Biol. Chem.* 270, 10125–10135 (1995); Garcia, P., Shoelson, S. E., Drew, J. S. and Miller, W. T., *J. Biol. Chem.* 269, 30574–30579 (1994); Gergel, J. R., McNamara, D. J., Dobrusin, E. M., Zhu, G., Saltiel, A. R., and Miller, W. T., *Biochemistry* 33, 14671–14678 (1994); Kage, R. K., Leeman, S. E. and Boyd, N. D., *J. Neurochem.* 60, 347–351 (1993); Kauer, J. C., Erickson-Vitanen, S. Wolfe, H. R. J. and DeGrado, W. F., *J. Biol. Chem.* 261, 10695–10700 (1986); Li, Y.-M., Marnerakis, M., Stimson, E. R. and Maggio, J. E., *J. Biol. Chem.* 270, 1213–1220 (1995a); Macdonald, S. G., Dumas, J. J. and Boyd, N. D., *Biochemistry* 35, 2909–2916 (1996); McNicoll, N., Escher, E. Wilkes, B. C., Schiller, P. W., Ong, H. and DeLean, A., *Biochemistry* 31, 4487–4493 (1992); Miller, W. T. and Kaiser, E. T., *Proc. Natl. Acad. Sci. USA* 85, 5429–5433 (1988); O'Neil, K. T., Erickson-Vitanen, S. and DeGrado, W. F.,*J. Biol. Chem.* 264, 14571–14578 (1989); Servant, G., Boulay, G., Bosse, R., Escher, E. and Guillemette, G., *Mol. Pharmacol.* 43, 677–682 (1993); Williams, K. P. and Shoelson, S. E., *J. Biol. Chem.* 268, 5361–5364 (1993); Zhang, Z.-Y., Walsh, A. B., Wu, L., McNamara, D. J., Dobrusin, E. M. and Miller, W. T., *J. Biol. Chem.* 271, 5386–5392 (1996)).

The large majority of receptors for bioactive peptides transduce signals through guanine nucleotide binding proteins. The question of which region(s) of a G-protein linked receptor interact with which region(s) of its peptide agonist has been difficult to approach. With neuropeptide ligands such as substance P (MW≈3 kDa), many contacts between ligand and receptor are involved as compared to much smaller non-peptide ligands. Thus, useful data from mutagenesis experiments are more difficult to acquire because of the extremely large number of mutants required for thorough analysis, and because mutations causing loss of function could reflect a change in receptor conformation distant from the binding site (Huang, R. R., Vicario, P. P., Strader, C. D. and Fong, T. M., *Biochemistry* 34, 10048–10055 (1995)). In contrast, photoaffinity labeling offers a uniquely powerful approach by directly identifying regions of the receptor in close contact with an identified amino acid of the agonist.

Photolabeling of substance P receptor (SPR, also known as NK-1R, a member of the G-protein coupled receptor family involved in pain modulation and inflammation (Pernow, B., *Pharmacol. Rev.* 35, 85–141 (1983); Otsuka, M. and Yoshioka, K., *Physiol. Rev.* 73, 229–308 (1993)) by a substance P (SP) analog is desirable for several reasons. SP, a member of the tachykinin peptide family, is a high affinity ligand (0.5–1 nM) with a single binding site on SPR. SPR has been cloned from several species (human, mouse, rat, and guinea pig) and shows a high degree of sequence homology between them (Gerard, N. P., Bao, L., He, X. P. and Gerard, C., *Regul. Peptides* 43, 21–35 (1993)), but expression levels remain low and purification is difficult. Mutagenesis studies of SPR have suggested that both extracellular and transmembrane domains are important for agonist binding (e.g., Cascieri, M. A., Macleod, A. M., Underwood, D., Shiao, L. L., Ber, E., Sadowski, S., Yu, H., Merchant, K. J., Swain, C. J., Strader, C. D and Fong, T. M., *J. Biol. Chem.* 269, 6587–6591 (1994); Fong, T. M., Huang, R. R. C. and Strader, C. D., *J. Biol. Chem.* 267, 25664–25672 (1992a); Fong, T. M., Yu, H., Huang, R. R. C. and Strader, C. D., *Biochemistry* 31, 11806–11811 (1992b); Fong, T. M., Cascieri, M. A., Yu, H., Bansal, A., Swain, C. and Strader, C. D., *Nature* 362, 350–353 (1993); Fong, T. M.,Yu, H., Cascieri, M. A., Underwood, D., Swain, C. J. and Strader, C. D., *J. Biol. Chem.* 269, 2728–2732 (1994a); Fong, T. M., Yu, H., Cascieri, M. A., Underwood, D., Swain, C. J. and Strader, C. D., *J. Biol. Chem.* 269, 14957–14961 (1994b); Gether, U., Johansen, T. E. and Schwartz, T. W., *J. Biol. Chem.* 268, 7893–7898 (1993a); Gether, U., Johansen, T. E., Snider, R. M., Lowe, J. A., III, Nakanishi, S. and Schwartz, T. W., *Nature* 368, 345–347 (1993b); Gether, U., Yokota, Y., Edmonds-Alt., X., Breliere, J. C., Lowe, J. A., III, Snider, R. M., Nakanishi, S., and Schwartz, T. W., *Proc. Natl. Acad. Sci. USA* 90, 6194–6198 (1993c); Gether, U., Edmonds-Alt., X., Breliere, J. C., Fuji, T., Hagiwara, D., Pradier, L., Garret, C., Johansen, T. E., and Schwartz, T. W., *Mol. Pharmacol.* 45, 500–508 (1994); Huang, R. R. C., Yu, H., Strader, C. D. and Fong, T. M., *Mol. Pharmacol.* 45, 690–695 (1994a); Huang, R. R. C., Yu, H., Strader, C. D. and Fong, T. M., *Biochemistry* 33, 3007–3013 (1994b); Jensen, C. J., Gerard, N. P., Schwartz, T. W. and Gether, U., *Mol. Pharmacol.* 45, 294–299 (1994); Sachais, B. S., Snider, R. M., Lowe, J. A., III and Krause, J. E., *J. Biol. Chem.* 268, 2319–2323 (1993); Yokota, Y., Akazawa, C., Ohkubo, H. and Nakanishi, S., *EMBO J.* 11, 3585–3591 (1992); Zoffman, S., Gether, U. and Schwartz, T. W., *FEBS Lett.* 336, 506–510 (1993).

Benzoylphenylalanine sparked a revolution in photoaffinity labeling (Dorman and Prestwich, 1994), but has the distinct disadvantage that the high specific activity radiolabel must be located distal to the photoactive residue in the primary structure. Furthermore, neither the BPA amino acid nor its PTH (phenylthiohydantoin) analog is detectable using standard amino acid analysis or Edman sequencing protocols (Kauer et al., 1986), making identification of the photoinsertion site difficult. Thus, there is a need for new photolabeling reagents which overcome these shortcomings.

SUMMARY OF THE INVENTION

Described herein is a new photolabeling reagent p-(4-hydroxybenzoyl)phenylalanine (HBPA) which overcomes many of the difficulties associated with BPA. Also described are its synthesis and its use in photolabeling. The hydroxyl group in the para position of HBPA results in a photoreactive amino acid which is detectable by protein sequencing and is amenable to radiolabeling with $^{125}I$, the radioisotope of choice in studies of peptide receptors. Photolabeling with a peptide incorporating HBPA into various positions allows the specific identification of the photoinsertion sites by radiosequencing, making purification-independent elucidation of peptide receptor binding sites now practical. Described here is the synthesis and characterization of p-(4-hydroxybenzoyl)phenylalanine in a form suitable for peptide synthesis, the incorporation of HBPA into the peptide substance P, radioLodination of the HBPA analogs of SP, and the photolabeling of substance P receptor using the peptide analogs.

The present invention is a (p-hydroxylbenzoyl) phenylalanine having a protected amine, a protected carboxylic acid, an activated carboxylic acid or a protected phenolic group. This compound can be incorporated into polypeptides for use in photolabeling other molecules, for example other peptides, proteins and nucleic acids. Polypeptides in which one or more (p-hydroxybenzoyl) phenylalanines have been incorporated can be used to photolabel molecules which form a complex with the polypeptide, e.g., have a $K_d$ less than about $10^{-6}$ M.

In one embodiment, the present invention is a compound represent by Structural Formula (I):

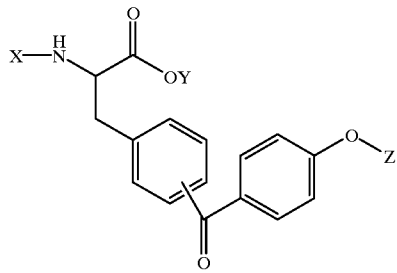

X is —H or an amine protecting group; —OY is —OH, an activating group for a carboxylic acid or a protecting group for a carboxylic acid; Z is —H or a phenolic protecting group, with the proviso that Z is not a straight chained, saturated alkyl group such as, for example, methyl or ethyl, and at least one of X, Y or Z is not —H. In a preferred embodiment, X is —H and —OY is a protecting group for a carboxylic acid. In another preferred embodiment, X is an amine protecting group and Y is —H.

Another embodiment of the present invention is a photoreactive polypeptide containing at least one (p-hydroxylbenzoyl) phenylalanyl group in the polypeptide chain, wherein the (p-hydroxylbenzoyl) phenylalanyl group is represented by Structural Formula (II):

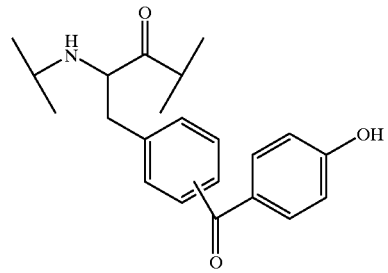

With respect to compounds represented by Structural Formulas (I) and (II), the p-hydroxylbenzoyl group is preferably in the para position. The invention includes the pure D stereoisomer, the pure L stereoisomer, mixtures thereof and racemic mixtures thereof. One or both phenyl rings in Structural Formulas (I) and (II) can be optionally substituted with ore or more substituents. Suitable substituents are those which: 1) do not interfere with the photolabeling reaction (e.g., the positions ortho to the —CO— group on each phenyl ring are generally unsubstituted) and 2) do not interfere with the formation of a complex between the photoreactive polypeptide and its target molecule, e.g., are generally small, sterically unhindered substituents. Preferably, at least one position ortho to the phenolic hydroxy group is unsubstituted to permit radiolabeling with radioactive iodine. Suitable substituents include C1–C4 straight chained or branched alkyl groups, halogens, aryl, substituted aryl, nitro or nitrile. Preferred substituents are radioactive isotopes such as $^{125}I$ and tritium.

Amine protecting groups are disclosed in Chapter 7 of Greene and Wuts, "Protective Groups in Organic Synthesis", John Wiley & Sons (1991), the teachings of which are incorporated herein by reference. Examples include R—CO— and RO—CO—, wherein R is an aliphatic group, a substituted aliphatic group, an aryl group and a substituted aryl group. Preferred amine protecting groups are those which are suitable for peptide synthesis are, for example, 9-fluorenylmethoxy carbonyl (F-MOC), t-butoxycarbonyl (t-BOC), benzyloxycarbonyl (CBZ), 9-(2-sulfo) fluorenylmethoxy carbonyl, 2-trimethylethoxy carbonyl, 2-phenylethoxy carbonyl, 1-(1-adamantyl)-1-methylethoxy carbonyl, 1,1-dimethyl-2-haloethoxy carbonyl, allyloxy carbonyl, furfuryloxycarbonyl, 2-bromoethyloxycarbonyl, 2-iodoethyloxycarbonyl, diisopropylmethyloxycarbonyl, cyclopentylmethyloxycarbonyl and 2-methyl-cyclohexyloxycarbonyl.

Carboxylic acid protecting groups are disclosed in Chapter 5 of Greene and Wuts, "Protective Groups in Organic Synthesis", John Wiley & Sons (1991), the teachings of which are incorporated herein by reference. Examples include R—O—, wherein R is as defined above. Preferred carboxylic acid protecting groups are those which are suitable for peptide synthesis are, for example, —O-t-butyl and —O-allyl.

Carboxylic acid activating groups are well known in organic synthesis and contain electron withdrawing groups so that $^-$OY is a good leaving group and is susceptible to substitution by nucleophilic reagents, e.g., —CO—OY+Nu$^-$ →—CO—Nu+$^-$OY. Carboxylic acid activating groups are often used in peptide synthesis for forming peptide bonds. Examples of suitable activating groups are prepared by forming the ester of pentafluorophenol, the ester of p-nitrophenol, the ester of di-nitrophenol and the ester of N-hydroxysuccinimide.

Phenolic protecting groups are well known in the art and are described :-n, for example, Chapter 3 of Greene and Wuts, "Protective Groups in Organic Synthesis", John Wiley & Sons (1991), the entire teachings of which are incorporated into this application by reference. Preferably, Z is a protecting suitable for use in peptide synthesis. Examples include the benzyl ether, the t-butyl ether and the allyl ether.

Aliphatic groups include straight chained or branched C1 to about C8 hydrocarbons, optionally with one or more units of unsaturation and/or with one to two heteroatoms (e.g., sulfur, oxygen and nitrogen) in the hydrocarbon chain. Thus, C2 to about C8 alkenes and alkynes are included within the meaning of the term "aliphatic group", as it is used herein. The term "aliphatic group" also includes C3 to about C8 cycloalkyl groups, optionally with one or more units of unsaturation and/or with one to three heteroatoms in the ring.

Aryl groups include carbocyclic aromatic groups, such as phenyl and naphthyl, and heteroaryl groups which do not interfere with peptide synthesis. Included are, for example, monocyclic or polycyclic aromatic groups containing one or more heteroatoms such as oxygen, nitrogen or sulfur. Examples of suitable monocyclic heteroaryl groups include thienyl, furanyl, pyrollyl, pyrimidinyl, pyrazolyl, thiazolyl and the like. A polycyclic heteroaryl group includes fused structures such as indolyl, benzimidazolyl, benzothiazolyl, benzothiophenyl, benzofuranyl, fluorenyl and benzopyranyl.

A "substituted aliphatic group" or a "substituted aryl group" can have one or more substituents which do not interfere with peptide synthesis, photolabeling or formation of a complex between the photoreactive polypeptide and its target molecule, depending upon where the substituent is located. Examples include halogens, alkyl groups, aryl groups, alkoxy groups, nitriles and nitro groups. In the present invention, commonly used substituents include alkyl groups such as methyl substituted with aryl groups (e.g., phenyl and fluorenyl).

Another embodiment of the present invention is a method of labeling a "target molecule" or "target compound". The method comprises providing a photoreactive polypeptide which forms a complex with the compound. The photoreactive polypeptide comprises at least one (p-hydroxylbenzoyl) phenylalanyl group in the polypeptide chain, wherein the (p-hydroxylbenzoyl) phenylalanyl group is represented by Structural Formula (II). The photoreactive polypeptide and the compound are mixed or incubated under conditions suitable for forming the complex. The complex is photolyzed under conditions suitable for reacting the compound and the photoreactive polypeptide, thereby labeling the target compound. "Labeling" a compound refers to forming a stable covalent bond between the (p-hydroxybenzoyl) phenylalanyl group (HBPA group) of the photoreactive polypeptide and a portion of the target compound which is either in contact or in close proximity with the HBPA group when the compound and the peptide form a complex. The labeled group in the compound can be identified by virtue of its bonding to the HBPA group, for example by amino acid sequencing.

A "complex" between the compound and photoreactive peptide involves non-covalent interactions which bind the compound and the peptide with sufficient affinity so that a covalent bond can be formed between the two molecules when photolyzed. Generally, compounds and photoreactive polypeptides which have a $K_d$ of $10^{-6}$ M or less bind with sufficient affinity.

Compounds which can be labeled by the methods disclosed herein include proteins which form complexes with peptides or other proteins. Examples include membrane bound receptors, intracellular receptors and proteins which catalyze biochemical reactions on other peptides or proteins. In this case, a suitable photoreactive peptide has an amino acid sequence corresponding to a peptide which binds the protein receptor or an amino acid sequence corresponding to a substrate for the target protein, with the exception that HBPA is substituted for one amino acid in the sequence. Preferably, the amino acid being substituted contacts or is in close proximity to a group in the target protein when a complex is formed between the target protein and the photoreactive polypeptide. The amino acid being substituted can be varied in order to map the site of the target protein (the "binding site") at which the photoreactive polypeptide binds in order to determine which amino acids in photoreactive polypeptide bind or are in close proximity to a given group in the binding site of the target protein.

Other biological molecules which bind polypeptides can also be labeled, for example, RNA, DNA and polysaccharides. To employ the labeling methods of the present invention, it is only required that 1) the amino acid sequence of a polypeptide which forms a complex with the target molecule be known so that a suitable photoreactive polypeptide for the target can be prepared and 2) suitable conditions for forming the complex between the target molecule and the photoreactive polypeptide be known.

Conditions suitable for forming a complex between a target molecule and a suitable photoreactive polypeptide depend on the target peptide. The skilled person will know of conditions suitable for forming such a complex for many target molecules. It is to be understood that the disclosed method will also be suitable for labeling target molecules not yet identified, once a polypeptide which forms a complex with the target and conditions suitable for forming said complex have been identified.

Photolyzing conditions suitable for reacting the photoreactive polypeptide and the target molecule are well known in the art and are disclosed in U.S. Pat. No. 4,762,881 and in the following references,(Adams, A. E., Pines, M., Nakamoto, C., Behar, V., Yang, Q. M., Bessalle, R., Chorev, M., Rosenblatt, M., Levine, M. A. and Suva, L. J., *Biochemistry* 34, 10553–105539 (1995); Behar, V., Pines, M., Nakamoto, C., Greenberg, Z., Bisello, A., Stueckle, S. M., Bessalle, R., Usdin, T. B., Chorev, M., Rosenblatt, M. and Suva, L. J., *Endocrinology* 137, 2748–2757 (1996); Blanton, M. P., Li, Y. M., Stimson, E. R., Maggio, J. E. and Cohen, J. B., *Mol. Pharmacol.* 46, 1048–1055 (1994); Bosse, R., Servant, G., Zhou, L.-M., Guillemette, G. and Escher, E., *Regul. Peptides* 44, 215–223 (1993); Boyd, N. D., Macdonald, S. G., Kage, R., Luber-Narod, J. and Leeman, S. E., *Ann. New York Acad. Sci.* 632, 79–93 (1991); Boyd, N. D., White, C. F., Cerpa, R, Kaiser, E. T. and Leeman, S. E., *Biochemistry* 30, 336–342 (1991); Boyd, N. D., Kage, R. K. and Leeman, S. E., The *Tachykinin Receptors* (Buck, S. H.,ed) pp. 219–236, Humana Press, Totowa, N.J. (1994); Boyd, N. D., Kage, R. K., Dumas, J. J., Krause, J. E. and Leeman, S. E., *Proc. Natl. Acad. Sci. USA* 93, 433–437 (1996); Gao, Z.-H, Zhi, G., Herring, B. P., Moomaw, Deogny, L., Slaughter, C. A. and Stull, J. T., *J. Biol. Chem.* 270, 10125–10135 (1995); Garcia, P., Shoelson, S. E., Drew, J. S. and Miller, W. T., *J. Biol. Chem.* 269, 30574–30579 (1994); Gergel, J. R., McNamara, D. J., Dohrusin, E. M., Zhu, G., Saltiel, A. R., and Miller, W. T., *Biochemistry* 33, 14671–14678 (1994); Kage, R. K., Leeman, S. E. and Boyd, N. D., *J. Neurochem.* 60, 347–351 (1993); Kauer, J. C., Erickson-Vitanen, S. Wolfe, H. R. J. and DeGrado, W. F., *J. Biol. Chem.* 261, 10695–10700 (1986); Li, Y.-M., Marnerakis, M., Stimson, E. R. and Maggio, J. E., *J. Biol. Chem.* 270, 1213–1220 (1995); Macdonald, S. G., Dumas, J. J. and Boyd, N. D., *Biochemistry* 35, 2909–2916 (1996); McNicoll, N., Escher, E. Wilkes, B. C., Schiller, P. W., Ong, H. and DeLean, A., *Biochemistry* 31, 4487–4493 (1992); Miller, W. T. and Kaiser, E. T., *Proc. Natl. Acad. Sci. USA* 85, 5429–5433 (1988); O'Neil, K. T., Erickson-Vitanen, S. and DeGrado, W. F., *J. Biol. Chem.* 264, 14571–14578 (1989); Servant, G., Boulay, G., Bosse, R., Escher, E. and Guillemette G., *Mol. Pharmacol.* 43, 677–682 (1993); Williams, K. P. and Shoelson, S. E., *J. Biol. Chem.* 268, 5361–5364 (1993); Zhang, Z.-Y., Walsh, A. B., Wu, L., McNamara, D. J., Dobrusin, E. M. and Miller, W. T., *J. Biol. Chem.* 271, 5386–5392 (1996)). The teachings of these references are incorporated herein by reference. Suitable conditions are also disclosed in the Experimental Section of this application.

Photoreactive peptides represented by Structural Formula (II) can be synthesized by known methods of peptide synthesis. For example, N-protected amino acids can be added onto the free N-terminus of a C-terminus blocked amino acid or peptide by solid phase peptide synthesis (e.g., BOC or FMOC method), by solution phase synthesis, or by other suitable techniques including combinations of the foregoing methods. Thus, compounds represented by Structural Formula (I) wherein X is an amine protecting group, —OY is —O or an activating group H and Z is —H or a phenol protecting can be incorporated into photoreactive polypeptides by these methods. The BOC and FMOC methods are established, widely used and are described in Merrifield, *J. Am. Chem. Soc.* 88:2149 (1963); Meienhofer, Hormonal Proteins and Peptides, C. H. Li, Ed., Academic Press, 1983, pp. 48–267; and Barany and Merrifield, in The Peptides, E. Gross and J. Meienhofer, Eds., Academic Press, New York, 1980, pp. 3–285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these references are incorporated herein by reference. Specific examples of preparing the peptides of the present invention are provided in the Experimental Section of this application.

Compounds represented by Structural Formula (I), wherein X is —H, —OY is a carboxylic acid protecting group or a carboxylic aced activating group and Z is —H or a phenol protecting group are also useful in peptide synthesis. These compounds can added onto the C-terminus of N-terminus protected peptides bound at the C-terminus to a polymer bound oxime by methods disclosed in Degrado and Kaiser, *J. Org. Chem.* 47:3258 (1982). These compounds can also added onto the C-terminus of N-terminus protected peptides bound at the C-terminus to a polymer bound hydroxymethylbenzoyl moiety by methods disclosed in Sheppard and Williams, *Int. J. Pept. Prot. Res.* 20:451 (1982). The teachings of these two references are incorporated herein by reference.

The invention is illustrated by examples in the following sections, which are not intended to be limiting.

DETAILED DESCRIPTION OF THE INVENTION

Experimental Procedures

Figure 1:
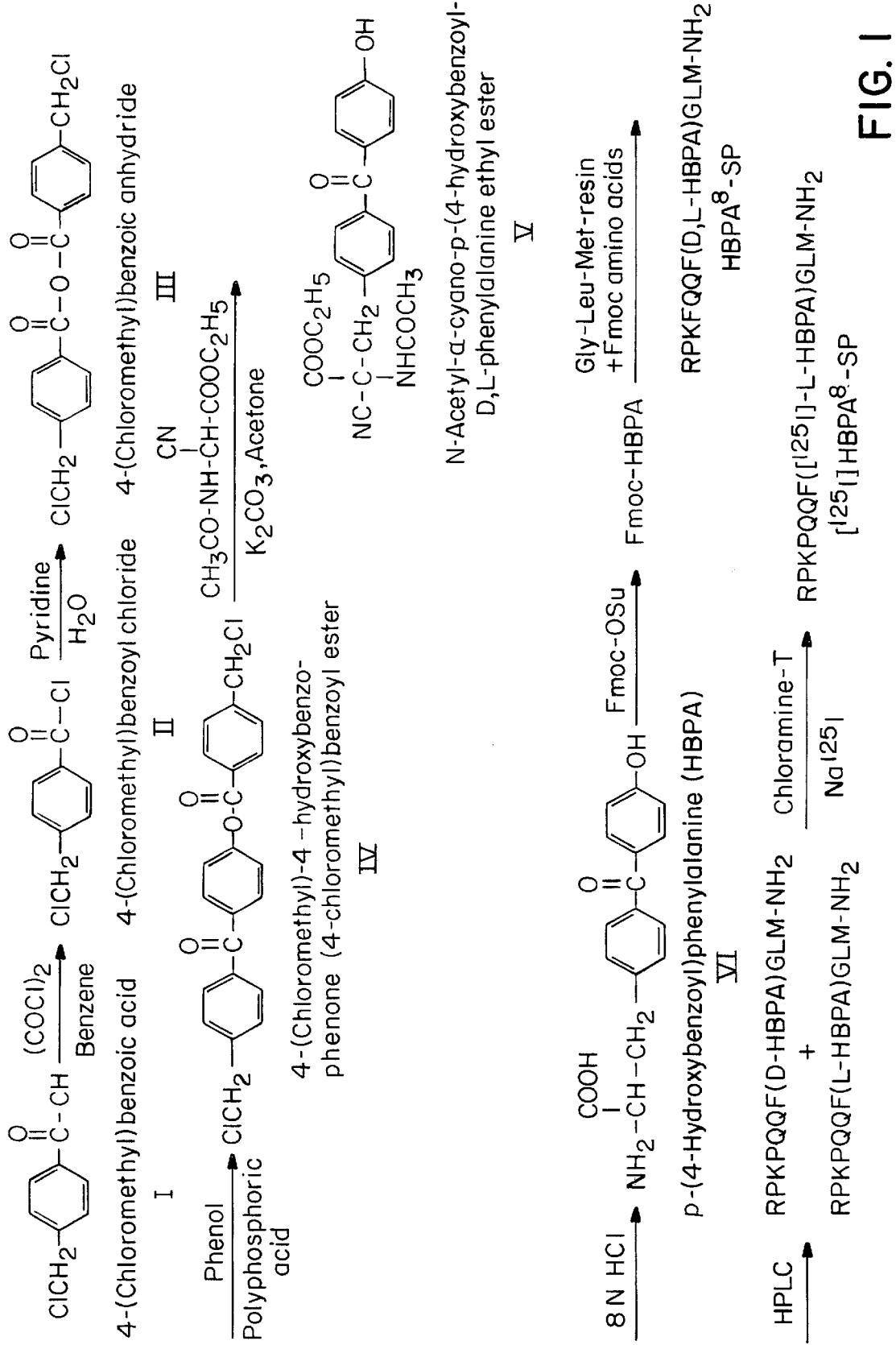
FIG. 1 is a schematic showing the synthesis of HBPA. 4-(Chloromethyl)benzoyl chloride (II) is made by refluxing 4-(chloromethyl)benzoic acid with oxalyl chloride in benzene. Mixing this compound with pyridine with gentle heating using a steam bath followed by ice quench gave 4-chloro-methylbenzoic anhydride (III). 4-Chloromethylbenzoic anhydride (III) is reacted with phenol in polyphosphoric acid to give the 4-chloromethylbenzoyl ester of 4-chloromethyl-4'-hydroxybenzophenone (IV). Reacting IV with ethylacetamidocyanoacetate and subsequent hydrolysis with concentrated HCl gives racemic p-(4-hydroxybenzoyl) phenylalanine (HBPA, VI). D,L-HBPA is derivatized using standard Fmoc chemistry for incorporation into the peptide (e.g., at position 8 of substance P) by solid-phase synthesis. Radioiodination of L-HBPA$^8$-SP is accomplished using Chloramine-T. See "Experimental Procedures" for details. HBPA can also be prepared by procedures disclosed in Horner and Medem., Chem. Ber., 85:520 (1952), the teachings of which are incorporated herein by reference.

Synthesis 4-(Chloromethyl)benzoyl chloride (II)—A mixture of 4-(chloromethyl)benzoic acid (I; 50 g, 0.29 mol) and oxalyl chloride (100 g, 0,79 mol) in anhydrous benzene (100 ml) was stirred at 25° C. and then refluxed for 2 h. Unreacted oxalyl chloride and benzene were removed by distillation. Traces of the remaining reagents were removed under reduced pressure to give 4-(chloromethyl)-benzoyl chloride (II) as a colorless liquid. The acid chloride was used in the next step without further purification.

4-(Chloromethyl)benzoic anhydride (III)—A solution of 4-(chloromethyl)benzoyl chloride (II; 14.2 g, 0.075 mol) in anhydrous pyridine (36 ml, 0.45 mol) was warmed gently over a steam bath for 10 min. The reaction mixture was poured over a slurry of ice (75 g) and concentrated HCl (37.5 ml). The solid residue was filtered under suction on a Buchner funnel and washed successively with three 6 ml portions of methanol followed by three 6 ml portions of benzene. The residue was dried under high vacuum to give 4-(chloromethyl)benzoic anhydride (III; 10.6 g, 88% yield).

(4-Chloromethyl)-4'-hydroxybenzophenone (4-chloromethyl)benzoyl ester (IV)—A mixture of the anhydride (III, 32.3 g, 0.1 mol) and phenol (3.76 g, 0.04 mol) in polyphosphoric acid (100 g) was stirred at 150° C. for 2 h. The mixture was cooled to 80° C. and poured over stirred crushed ice (500 g). The resulting precipitate was filtered on a Buchner funnel and thoroughly washed with water. The solid was suspended in water (400 ml) and the pH adjusted to 7.0 under vigorous stirring with 10 M NaOH. After stirring for 4 h, the suspension was extracted twice with 300 ml portions of chloroform (NaCl was added to separate the phases. The combined chloroform extracts were taken to dryness on a rotary evaporator. The residue was stirred in benzene (50 ml) and filtered. The solution was evaporated on a rotary evaporator and the residue dried under high vacuum to give 10.4 gram of solid. Analytical thin layer chromatography of the product (silica gel, benzene) showed two major spots with R$_f$ 0.14 and 0.41 which were identified as (4-chloromethyl)-4'-hydroxybenzophenone (4-chloromethyl)benzoyl ester (IV) and phenyl-(p-chloromethyl)benzoate, respectively, by NMR.

The crude solid was suspended in benzene:hexane 1:1 v/v (100 ml), heated and decanted after cooling. The supernatant was applied to a column of silica gel G (70 g) equilibrated with benzene:hexane 1:1 to separate the benzophenone derivative from the phenylbenzoate contaminant. The column was eluted with the same solvent (250 ml), followed by benzene:hexane 3:1 (350 ml) and finally with benzene. Fractions (50 ml) were collected. Fractions containing the component with R$_f$ 0.14 (silica gel plate developed with benzene) were pooled and dried on a rotary evaporator. The residue (2.4 g; 15% yield based on starting phenol) was recrystallized from absolute ethanol to give 2.2 g of colorless needles (m.p. 137–138° C.).

Assignments for the NMR spectrum (CDCl$_3$) were made by inspection. The spectrum was consistent with the structure for the product (4-chloromethyl)-4'-hydroxybenzophenone (4-chloromethyl)benzoyl ester (IV) having chemical shifts d (ppm downfield from internal tetramethylsilane) of 4.65 (ClCH$_2$—), 7.54 (H-3 of both the hydroxybenzophenone and the benzoyl ester rings3), 8.22 (H-2 of the benzoyl ester ring), and 7.36 (H-2), 7.91 (H-2'), and 7.82 (H-3') of the hydroxybenzophenone ring. Elemental analysis of IV (66.4% C, 4.0% H, 16.7% Cl) was consistent with the proposed structure C$_{22}$H$_{16}$O$_3$Cl$_2$.

N-Acetyl-a-cycano-4-hydroxybenzoyl-D,L-phenylalanine ethyl ester (V)—A stirred mixture of (4-chloromethyl)-4'-hydroxybenzophenone (4-chloromethyl)benzoyl ester (IV, 798 mg, 2 mmol), ethylacetamidocyanoacetate (701 mg, 4.12 mmol), potassium carbonate (382 mg, 2.76 mmol), and potassium iodide (8.3 mg, 0.05 mmol) in acetone was refluxed in the dark under argon for 20 h. After cooling, the solid precipitate was filtered and washed with acetone. TLC (chloroform:ethanol 94:6) showed a major spot with R$_f$ 0.24 and several minor spots. The crude product was purified by preparative TLC to give 360 mg (47% yield) of a glassy solid.

The NMR spectrum (CDCl$_3$) for the product was consistent with the structure for N-acetyl-a-cyano-4-hydroxybenzoyl-D,L-phenylalanine ethyl ester (V) . [The phenolic ester resulting from the SN$_2$ reaction was probably saponified during the overnight alkaline reflux.] Chemical shifts d (ppm): 7.64, 7.04 (H-3 of the phenylalanine and hydroxybenzoyl rings, respectively), 7.89 (H-2, H-2'), 4.32 (—CH$_2$—), 2.14 (—NHCOC$\underline{H}_3$) , 3.49 (—OC$\underline{H}_2$ CH$_3$), and 1.32 (—OCH$_2$C$\underline{H}_3$). Elemental analysis of V (63.3% C, 5.1% H, 7.2% N) was consistent with the proposed structure C$_{21}$H$_{20}$NO$_5$.

p-(4-Hydroxybenzoyl)-D,L-phenylalanine (HBPA) (VI)— The crude reaction product from the above reaction (TLC-purification resulted in loss of material, apparently because the crude material also contained the phenolic ester of N-acetyl-a-cyano-p-(4-hydroxybenzoyl) -D,L-phenylalanine, V) was suspended in 8 M HCl (5 ml) and refluxed under argon in the dark for 20 h. After drying on a rotary evaporator, the residue was suspended in water (10 ml) and the pH adjusted to 7.0 with 1 M NaOH. After vigorous stirring for 1 h, the precipitate was filtered and washed with water. The dried precipitate was resuspended in ethanol (15 ml) and heated to boiling. After cooling, the precipitate was filtered, washed with ethanol and dried under high vacuum to give 427 mg (75% yield based on the 4-(chloromethyl)-4'-hydroxybenzophenone (4-chloromethyl)benzoyl ester, IV) of p-(4-hydroxybenzoyl) phenylalanine (VI). TLC (silica gel, butanol:acetic acid:water 4:1:5) showed one spot with $R_f$ 0.5.

The chemical shifts d (ppm) determined by NMR spectroscopy (CDCl$_3$) for the product were 7.49, 7.72 (H-2, H-3 of the phenylalanine ring), 7.76, 6.91 (H-2, H-3 of the hydroxybenzoyl ring), 3.80 ($C_aH$), and 3.10, 3.40 ($C_bH_2$). These results are consistent with the structure of the final product p-(4-hydroxybenzoyl)phenylalanine (VI). Elemental analysis (65.8% C, 5.4% H, 4.8% N) and mass spectrometry (ESIMS; (M+1)$^+$ of 286.1) were consistent with the proposed structure $C_{16}H_{15}NO_4$.

N-Fmoc-p-(4-hydroxybenzoyl)-D,L-phenylalanine—p-(4-Hydroxybenzoyl)phenylalanine (1.4 mmol) was dissolved in 5 ml 10% sodium bicarbonate and treated with Fmoc-OSu (1.4 mmol) in acetone (5 ml) for 18 h. Thin layer chromatography (silica gel, dichloromethane:methanol:acetic acid 93:5:2; $R_f$=0.3) showed the reaction to be ≧95% complete. Acetone was removed by evaporation. The clear yellow aqueous solution was diluted to a final volume of 25 ml and extracted with ether (2×20 ml). Ethyl acetate was added and the mixture was acidified to pH about 2. The organic phase was evaporated and the residue was coevaporated with clichloromethane (2×50 ml). The solid obtained was crystallized from dichloromethane (30 ml). The yield was 92%.

The NMR spectrum (CDCl$_3$) was consistent with the structure of the final product N-Fmoc-p-(4-hydroxybenzoyl) phenylalanine. The chemical shifts d (ppm) for the aromatic protons are almost identical (all within 0.01 ppm) to those for the underivatized amino acid. The chemical shift d (ppm) for $C_aH$ shifted to 4.40, and for $C_bH_2$ shifted only slightly to 3.10 and 3.34. For the Fmoc group, the chemical shifts d (ppm) were 6.19 (H-1), 7.36 (H-3, H-12), 7.67 (H-4, H-5, H-10, H-11), 7.45 (H-6, H-9), and 4.25 (—CH$_2$OCO—).

Mass spectrometry (CIMS) gave an (M+1)$^+$ of 507.5 as expected for Fmoc-HBPA. The extinction coefficient for Fmoc-HBPA at 300 nm was determined by absorbance spectroscopy to be 18,700 cm$^{-1}$M$^{-1}$ in acetonitrile:dimethylsulfoxide 3:1.

Figure 5:
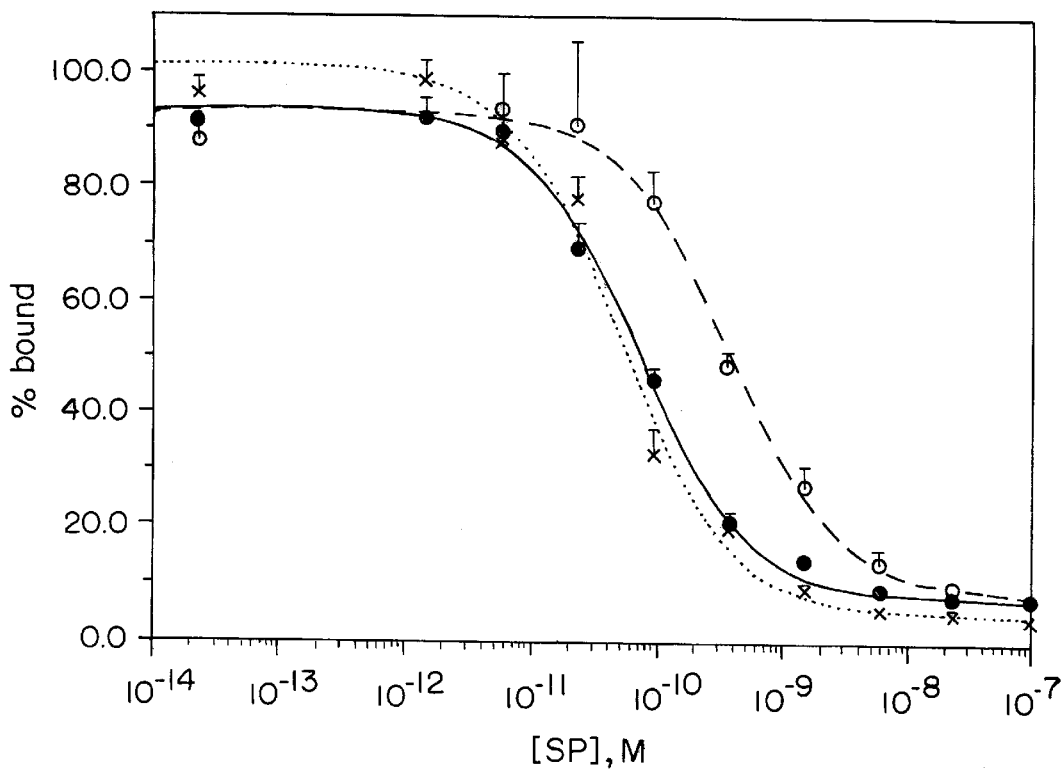
FIG. 5 is a graph showing the binding of HBPA$^8$-SP to anti-substance P antibody. [$^{125}$I]BHSP was displaced from substance P antibody by the D- and L-diastereomers of HBPA$^8$-SP. (-●-) L-HBPA$^8$-SP binds to the antibody with a higher affinity than (-○-) D-HBPA$^8$-SP. The IC$_{50}$ for L-HBPA$^8$-SP is 52±8 pM which is very similar to that determined for SP (71±6 pM; (-x-)). The IC$_{50}$ measured for the D-isomer is significantly larger (about 8x) at 390±40 pM. Anti-substance P antibody was used at a dilution of 1/160,000; [$^{125}$I]BHSP=3.3 pM. IC$_{50}$ is expressed as the mean±standard deviation of ≧3 experiments.
Figure 6:
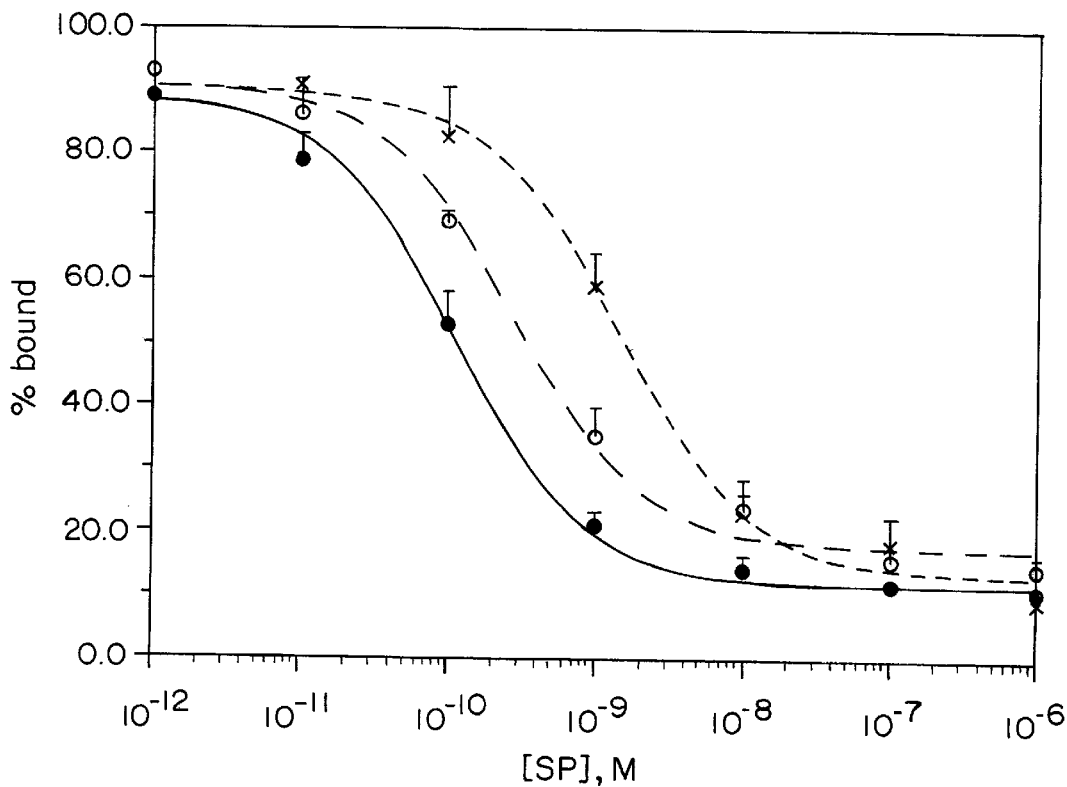
FIG. 6 is a graph showing the binding of [$^{125}$I]HBPA$^8$-SP to SPR. After pre-incubation on ice with protease inhibitors and BSA, the cells (about 1×10$^6$ cells/sample) were incubated for 2 h on ice with tracer (25 pM [$^{125}$I]-L-HBPA$^8$-SP (-●-) or [$^{125}$I]BHSP) (-○-)) and displaced by SP, or with 25 pM [$^{125}$I]BHSP and displaced by D-HBPA$^8$-SP (-x-). Percentage of tracer bound was determined by solubilization and counting after washing away excess unbound tracer. IC$_{50}$ for displacement by SP of [$^{125}$I]-L-HBPA$^8$-SP is 0.11±0.01 nM and of [$^{125}$I]BHSP is 0.28±0.07 nM, and for displacement by D-HBPA$^8$-SP of [$^{125}$I]BHSP is 1.50±0.34 nM. The data shown is the average of four experiments containing triplicate samples in each. IC$_{50}$ is expressed as the mean±standard deviation of ≧4 experiments.

L-HBPA$^8$-substance P—The peptide synthesis of the SP analog (HBPA$^8$-SP) ArgProLysProGlnGlnPhe(L-HBPA)GlyLeuMet-NH$_2$ was performed using a standard Fmoc solid-phase synthetic strategy (Maggio, J. E., Stimson, E. R., Ghilardi, J. R., Allen, C. J., Dahl, C. E., Whitcomb, D. C., Vigna, S. R., Vinters, H. R., Labenski, M. E., and Mantyh, P. W., Proc. Natl. Acad. Sci. USA 89, 5462–5466 (1992)). The crude synthetic peptide was HPLC purified using a Synchrom C$_{18}$ column (250×4.6 mm). The crude racemic peptide D,L-HBPA$^8$-SP had two major UV-absorbing (215 nm) peaks of approximately equal intensity (FIG. 2) eluting at 51.0 and 54.4 % acetonitrile. Peptide diastereomers containing D- or L-HBPA were identified as described for previous work with D,L-isomers of BPA (Li, Y.-M., Marnerakis, M., Stimson, E. R., and Maggio, J. E., J. Biol. Chem. 270,1213–1220 (1995a)). The L-HBPA$^8$-SP elutes earlier than D-HBPA$^8$-SP on RP-HPLC (Li et al., 1995a; Blanton et al., 1994). The first peak was more active than the second with both a SP specific antibody and SPR, as expected for the L-diastereomer (FIGS. 5, 6). HBPA$^3$-SP was prepared in the same manner but with HBPA substituted for lysine (SP position 3). The isolated L-HBPA$^8$-SP was analyzed for purity and correct structure by amino acid analysis, mass spectroscopy, and amino-terminal sequencing. The peptide sequence was confirmed by Edman sequencing and mass spectrometry (MALDMS) gave m/z 1467 [(M+1)$^+$] as expected. The PTH derivative of HBPA eluted from the sequencer column under standard conditions at 15.3 min (FIG. 3). The extinction coefficient for the peptide (L-HBPA$^8$-SP) was determined to be 16,600 cm$^{-1}$M$^{-1}$ at 292 nm in acetonitrile:dimethylsulfoxide (6:1) by absorbance spectroscopy, using amino acid analysis for quantitation of the peptide. Like BPA (Li et al., 1995a), HBPA was not detected by conventional amino acid analysis (ion-exchange using post-column ninhydrin detection), but the remaining amino acids gave the expected molar ratios for SP with HBPA substituted for Phe$^8$ [Arg$^{1.03}$ (1), Pro$^{2.07}$ (2), Lys$^{1.03}$ (1), Gln$^{2.14}$ (2), Phe$^{1.08}$ (1), Gly$^{1.05}$ (1), Leu$^{1.04}$ (1), Met$^{0.87}$ (1)].

Radioiodination of HBPA$^8$-SP—The radioligand [$^{125}$I]-L-HBPA$^8$-SP was prepared using general peptide iodination techniques previously described (Too, H.-P. and Maggio, J. E., Methods Neurosci. 6, 232–247 (1991)). Typically, 10 nmol of dry peptide was dissolved in 50 μl of 0.5 M borate buffer, pH 8.0, and vortex-mixed with 1 mCi of Na$^{125}$I (10 μl; Amersham IMS-30). Chloramine-T (10 μg) was added and the mixture was vortex-mixed for 90 sec before the reaction was quenched with 100 μg of Na$_2$S$_2$O$_5$. To separate the peptide from free $^{125}$I, the mixture was diluted and acidified with 0.525 ml of 60 mM trifluoroacetic acid (TFA), with the addition of 25 μl of 2% bovine serum albumin solution to limit nonspecific adsorption. The mixture was then applied to an activated C$_{18}$ Sep-Pak cartridge (Waters) and the iodide and peptide were eluted from the cartridge with a series of 0.5 ml portions of 10 mM TFA in increasing alcohol (ethanol:methanol, 1:1) content. The iodide eluted immediately, whereas the peptide was retained until the alcohol content reached about 60%. The peptide fractions (containing both oxidized and reduced methionine), eluting with 60–90% alcohol, were pooled and reduced in volume under a nitrogen stream. After the addition of 20% (v/v) 2-mercaptoethanol, the sample was heated at 90° C. for 2 h to reduce methionine sulfoxide to native methionine. Further purification was achieved by reverse phase HPLC on a Vydac C$_{18}$ column. The eluate was collected in fractions during shallow acetonitrile gradient elution and the fractions counted for radioactivity. The reduced (methionine) monoiodinated (HBPA) peptide eluted in a well-resolved peak (at 32% acetonitrile), predictably later than the original unlabeled peptide (at 30% acetonitrile) or the oxidized products, but prior to the reduced diiodinated peptide. The reduced monoiodinated [$^{125}$I]HBPA$^8$-SP (specific activity is approximately 2000 Ci/mmol; 1 Ci=37 GBq) was protected from oxidation with 0.5% (v/v) 2-mercaptoethanol added immediately after purification and stored at −20° C. until use. The amount of free $^{125}$I in the final tracer was determined by quantitative separation of free $^{125}$I and the $^{125}$I-peptide using an activated C$_{18}$ Sep-Pak cartridge (Waters) as described above. The complete synthetic scheme is shown in FIG. 1. HBPA$^3$-SP was synthesized, purified, and radiolabeled using the same method as described above.

Biochemical Procedures

Radioimmunoassay for D-HBPA$^8$-SP and L-HBPA$^8$-SP—Anti-SP antibody (Too, H.-P., Cordova, J. L. and Maggio, J.

E., *Peptides* 10, 25–30 (1989)), [$^{125}$I]BHSP, and D- or L-HBPA$^8$-SP were incubated in RIA buffer (50 mM sodium phosphate buffer, pH 7.5, with 0.1% BSA and 1 mM sodium azide) in a total volume of 0.4 ml. The titer of the antibody was determined by incubating 3.3 pM [$^{125}$I]BHSP with the anti-SP antibody in RIA buffer overnight at 4° C. Assays were worked up at 4° C. by adding 0.5 ml activated charcoal suspension (20 g/L activated charcoal in 50 mM sodium phosphate, pH 7.5, 10% heat-inactivated human serum, 1 mM sodium azide), incubating for 15 m, and centrifuging at 3000 g for 15 min to separate bound tracer (supernatant) from free tracer (charcoal pellet). The displacement curve for HBPA$^8$-SP was determined at 1/160,000 antibody titer with 3.3 pM [$^{125}$I]BHSP and L-HBPA$^8$-SP or D-HBPA$^8$-SP with incubation at 4° C. overnight. The assay was worked up as described above.

Curve fitting was performed using the following equation:

$$B = T_b * (1/(1+L/IC_{50})) + N_b$$

where B is the percent binding, $T_b$ is the percent total binding, L is the ligand concentration, $IC_{50}$ is the concentration at which 50% of the binding is displaced, and $N_b$ is the percent nonspecific binding.

Binding Studies of [$^{125}$I]HBPA$^8$-SP—P388D$_1$ cells (a nontransfected murine macrophage/monocyte cell line (Dawe, C. J., and Potter, M., *Am. J. Pathol.* 33, 603 (1957)), that express a high density of functional SP receptors (Li, Y.-M., Marnerakis, M., Stimson, E. R. and Maggio, J. E., *J. Biol. Chem.* 270, 1213–1220 (1995a); Li, Y. -M., Wingrove, D. E., Too, H. P., Marnerakis, M., Stimson, E. R., Strichartz, G. R. and Maggio, J. E., *Anesthesiology* 82, 166–173 (1995b)) but no detectable levels of other tachykinin receptors (H.-P. Too and J. E. Maggio, unpublished results)) were inoculated (5×10$^5$ cells/well) on FBS precoated 24-well plates and cultured overnight in Dulbecco's modified Eagle's medium (DMEM) with 10% FBS. Protease inhibitors (0.004% bacitracin, 0.0002% chymostatin, 0.0004% leupeptin) and 0.1% BSA was added to the confluent cells (approximately 1×10$^6$ cells/well in DMEM and 10% FBS) and incubated for 30 min at room temperature (25° C.). The cells were then washed twice (0.5 ml/well) with ice-cold buffer (DMEM+20 mM HEPES, pH 7.2) and incubated with 0.5 ml of buffer on ice for at least 10 min in the presence of protease inhibitors and 0.1% BSA. The radioactive ligand ([$^{125}$I]HBPA$^8$-SP or [$^{125}$I]BHSP), in the presence or absence of unlabeled SP, CP-96,345 (a nonpeptide NK-1R antagonist), or D-HBPA$^8$SP was added to a final concentration of 25 pM (approximately 8×10$^4$ cpm/ml) and incubated for 2 h. Nonspecific binding is defined as binding in the presence of 10 mM SP. After incubation, the cells were washed twice with 0.5 ml/well phosphate-buffered saline (104 mM NaCl, 2.7 mM KCl, 10 mM Na$_2$HPO$_4$, 1.8 mM KH$_2$PO$_4$, pH 7.2), then solubilized by 0.5 ml lysis buffer (1% Nonidet P-40, 0.2% SDS, 150 mM NaCl, 50 mM Tris, pH 8.0) for 20 min and transferred for gamma counting. Unlabeled SP was stored as 10 mM stock solutions in dimethylsulfoxide. Curve fitting was performed as described above. Binding studies were also performed with [$^{125}$I] HBPA$^3$-SP.

Photolabeling of SPR in P388D$_1$ cells with [$^{125}$I]HBPA$^8$-SP—Photolysis was performed as previously described (Li et al., 1995a; Blanton et al., 1994) with the following modifications. P388D$_1$ cells (5×10$^6$ cells/5 ml) were inoculated on FBS-pretreated dishes (60 mm) in DMEM with 10% FBS and grown overnight. The cultured cells (approximately 1×10$^7$) were incubated with protease inhibitors and 0.1% BSA for 30 min at room temperature (25° C.). The cells were then washed twice (5 ml) with ice-cold buffer (DMEM+20 mM HEPES, pH 6.7) and incubated with 5 ml of buffer on ice for at least 10 min, in the presence of protease inhibitors, and 0.1% BSA. The photolabile radioligand, in the presence or absence of unlabeled SP or CP-96,345, was added to a final concentration of 2 nM (approximately 6×10$^6$ cpm/ml) and incubated 2 h at 4° C. The dishes were then frozen by placement on crushed dry ice. The frozen sample was irradiated under nitrogen for 2 h using a focused HBO 100-watt mercury short arc lamp through an optical filter to eliminate light below 310 nm. A second filter removed infrared wavelengths (>900 nm) to minimize sample heating during photolysis (Li et al., 1995a). Alternatively, the sample can be irradiated in a commerical photoreactor at 3500 Å.

After photolysis, the sample was thawed and any remaining attached cells were scraped from the bottom of the plate. The sample was transferred to microfuge tubes and centrifuged at 16,000 g for 30 min. The pelleted cells were hypotonically lysed by resuspending in 0.3 ml of 5 mM Tris-HCl, pH 8.0, for 15 min at room temperature. Then the samples were homogenized and centrifuged at 500 g for 15 min to remove debris. The resulting supernatants were sedimented at 16,000 g for 30 min and the membrane pellets stored at −20° C. until analysis. These experiments have also been performed with [$^{125}$I]HBPA$^3$-SP, giving similar results.

To confirm that [$^{125}$I]HBPA photocrosslinked to an amino acid of a target protein could be released during Edman sequencing as the PTH derivative, a 10% BSA solution was photolabeled with [$^{125}$I]HBPA$^3$-SP for 15 min on ice, digested with *Staphylococcus aureus* V8 protease, and the HPLC-purified labeled fragment sequenced by Edman degradation.

Sequence Analysis—Amino-terminal sequence analysis was performed with an Applied Biosystems model 477A protein sequencer, using gas phase cycles. Samples of HPLC-purified radioiodinated and non-iodinated HBPA$^8$-SP were mixed and immobilized on chemically modified, glass fiber filter discs (Beckman Instruments) rather than polybrene-treated filters to improve sequencing yields of hydrophobic peptides (Pedersen, S. E., Sharp, S. D., Liu, W.-S. and Cohen, J. B., *J. Biol. Chem.* 267, 10489–10499 (1992)). [$^{125}$I]HBPA$^3$-SP and the labeled fragment from V8 enzymatic digests of [$^{125}$I]HBPA$^3$-SP photocrosslinked to BSA were sequenced in the same manner. Initial yield ($I_o$) and repetitive yield (R) were calculated by nonlinear, least-squares regression of the observed release (M) for each cycle (n) using the equation $M = I_o R^n$.

Miscellaneous—SDS-PAGE was performed on 10% acrylamide gels according to Laemmli, U. K., *Nature* 227, 680–685 (1970). V8 protease digests of proteins were performed as described in Li et al. (1995a). Mass spectroscopy of HBPA and Fmoc-HBPA was performed using a Finnegan TSQ700 triple quadrupole mass spectrometer. NMR spectra were recorded using a Varian Unity Spectrometer at 500 MHz in CDCl$_3$ using tetramethylsilane as an internal standard.

RESULTS

Synthesis and Characterization of HBPA—HBPA (VI) was successfully synthesized (FIG. 1) in three steps from 4-(chloromethyl)benzoic anhydride (III). The Friedel-Crafts condensation of 4-(chloromethyl)benzoic anhydride (III) and phenol in polyphosphoric acid produced (4-chloromethyl)-4-hydroxybenzophenone esterified with (4-chloromethyl)benzoic acid (IV). The reaction of the ester intermediate with ethylacetamidocyanoacetate under alkaline conditions resulted in the expected reaction with the cyano compound accompanied by the hydrolysis of the ester to give the major product (V). Acid hydrolysis of the cyano intermediate (V) yielded the p-(4-hydroxybenzoyl) phenylalanine (VI) photoprobe. The amino acid analog was coupled for peptide synthesis using standard Fmoc strategy. Results from both NMR spectroscopy and elemental analysis on the intermediates (IV, V) and the final product (VI) were consistent with those expected for the compounds and confirmed using appropriate standards. Mass spectrometry on HBPA (VI), Fmoc-HBPA, L-HBPA$^8$-SP, and L-HBPA$^3$-SP gave the expected (M+1) peaks (286.1, 507.5, 1467, and 1487, respectively).

The synthesis of HBPA was first attempted by the route previously described for preparation of BPA (chlorination of the methyl group of p-methyl benzophenone; Kauer, et al. (1986)) and by several similar routes. All these routes failed due to the chlorination of the aromatic ring rather than the desired chlorination of the methyl group of the various starting materials.

Figure 2:
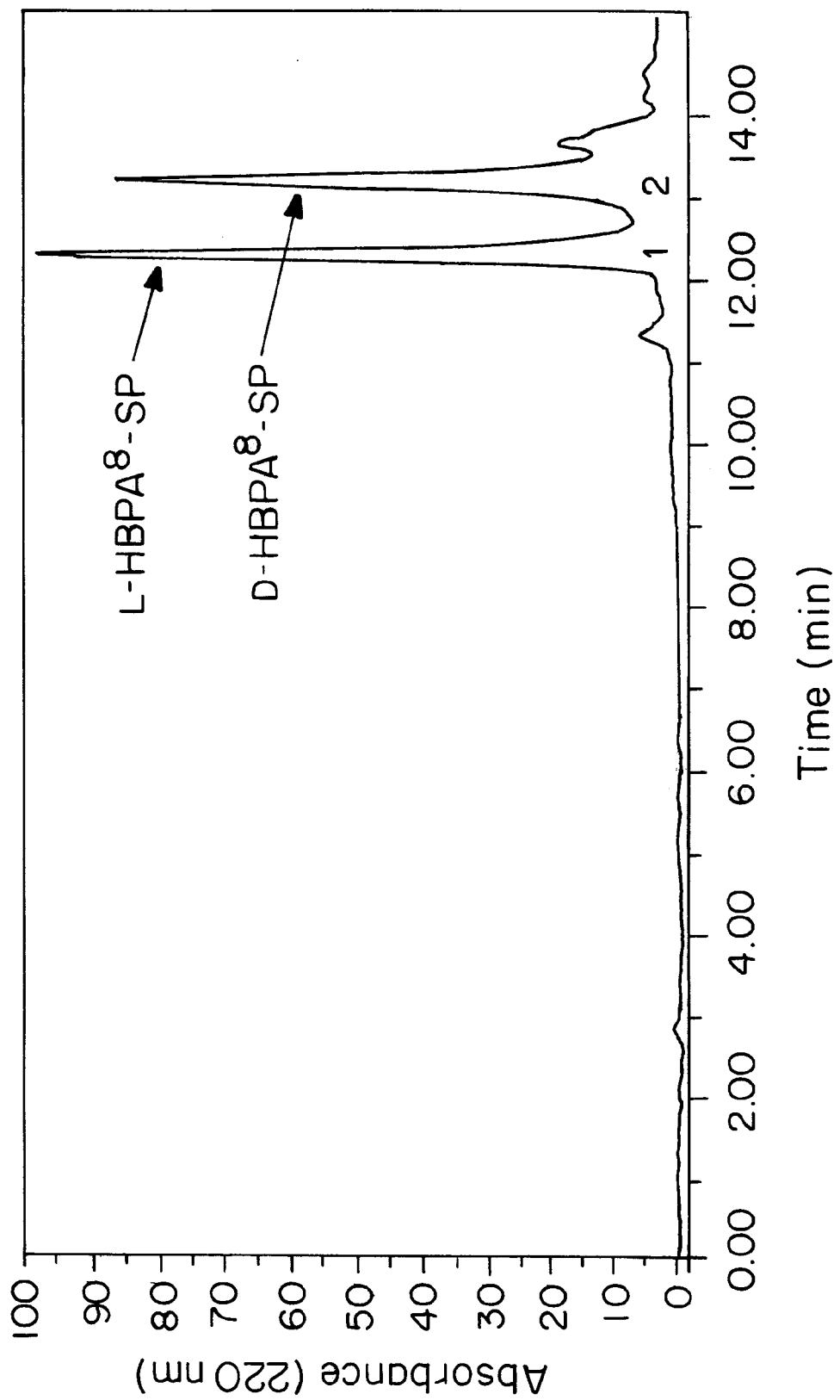
FIG. 2 is an HPLC chromatogram showing HPLC purification of HBPA$^8$-SP. The crude synthetic peptide Arg-ProLysProGlnGlnPhe (D,L-HBPA)GlyLeuMet-NH$_2$ was purified by HPLC on a Synchrom C$_{18}$ (250×4.6 mm) column with a flow rate of 1.5 ml/min using a 5–65% acetonitrile gradient. The L-HBPA$^8$-SP diastereomer elutes at 51.0% acetonitrile and the D-HBPA$^8$-SP diastereomer elutes at 54.4% acetonitrile. The synthesis produced a racemic mixture consisting of 43.5% L-HBPA$^8$-SP, 44.7% D-HBPA$^8$-SP (quantitated by integration of UV peaks), and minor contaminants. Purification by HPLC produced optically pure L-HBPA$^8$-SP and optically pure D-HBPA$^8$-SP.
Figure 3A:
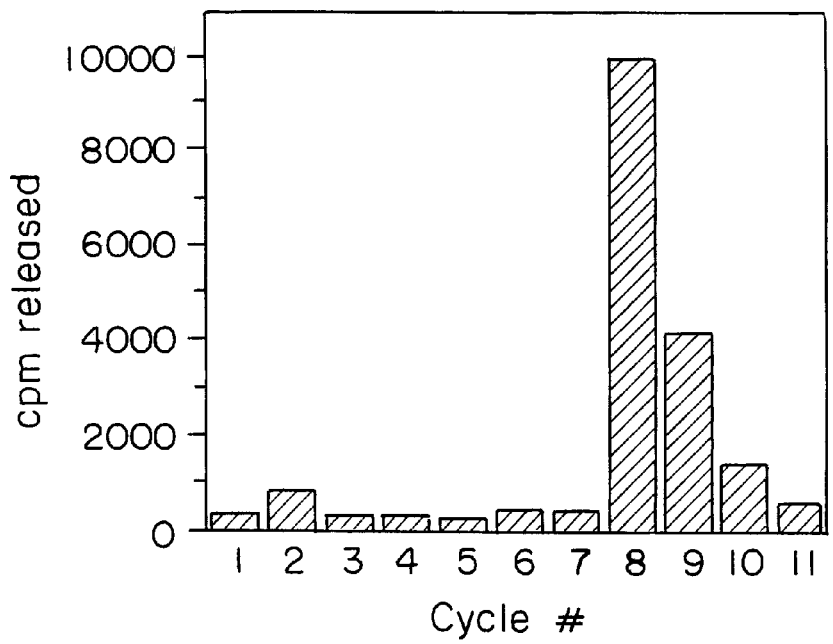
FIG. 3a is a histogram showing sequence analysis of an HBPA$^8$-SP peptide. The counts from the peptide [$^{125}$I] HBPA$^8$-SP are released in cycle #8, corresponding to the HBPA amino acid, as expected.
Figure 3B:
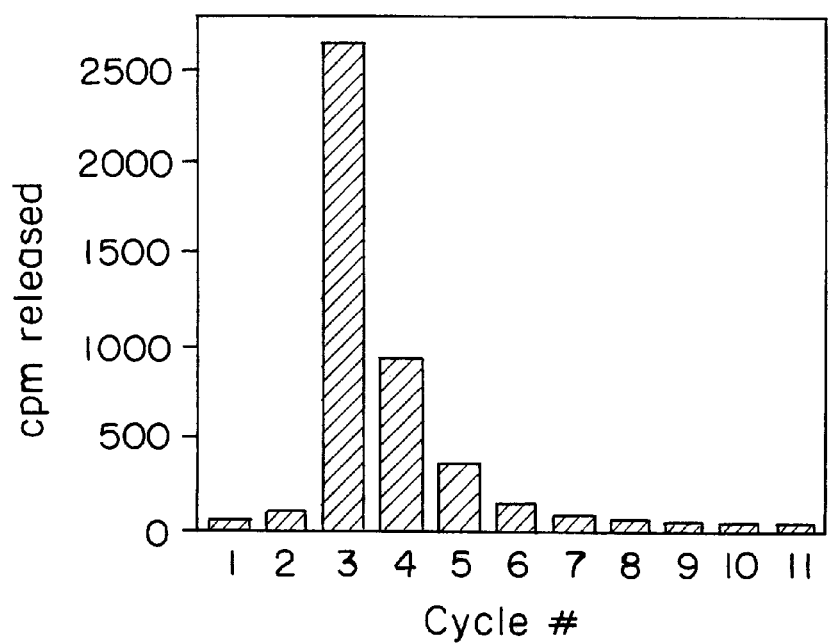
FIG. 3b is a histogram showing sequence analysis of an HBPA$^3$-SP peptide. The counts from [$^{125}$I]HBPA$^3$-SP are released in cycle #3, corresponding to the HBPA amino acid, as expected.

The amino acid analog (HBPA) was easily incorporated into positions 3 arid 8 of the neuropeptide substance P by standard solid-phase synthesis. Both D,L-HBPA$^8$-SP and D,L-HBPA$^3$-SP were synthesized; separation of the diastereomers was easily accomplished using RP-HPLC (FIG. 2). The identities of the peptides were confirmed by amino acid analysis, sequencing (FIG. 3), immunochemistry (FIG. 5), and receptor binding (FIG. 6). Radioiodination of the L-diastereomer at the HBPA amino acid was accomplished using Chloramine-T and confirmed by sequencing of the radiolabeled peptide. Sequencing of [$^{125}$I]HBPA$^8$-SP both before and after photolysis showed the majority of the counts associated with cycle #8 with a slight lag in cycles #9 and #10 (FIG. 3a). Edman degradation of [$^{125}$I]HBPA$^3$-SP resulted in a major release of counts in cycle #3 (FIG. 3b), as expected. To show feasibility of the proposed method of analysis, a concentrated solution of BSA (10%) was photolabeled with [$^{125}$I]HBPA$^3$-SP. The photolabel inserted into a single site as determined by both SDS-PAGE and RP-HPLC after V8 enzymatic digestion of the sample, and subsequently by sequencing. This experiment demonstrated the ability of the HBPA•amino acid adduct to be released in sequencing as a PTH derivative. The PTH derivative of the photo inserted HBPA•BSA adduct is released in cycle #4 (FIG. 3c), demonstrating the potential utility of this method in mapping binding sites. PTH-HBPA was observed under standard Edman sequencing conditions at 15.3 min (FIG. 4), between valine and tryptophan. In contrast, PTH-BPA was not detectable (Li et al., 1995a; Blanton et al., 1994). After radioiodination, the peptides were stable for both binding and photolabeling studies for more than a month. Additionally, the amount of free iodide present after one month of storage at −20° C. was less than 1%.

Binding Studies with [$^{125}$I]HBPA$^3$-SP—The binding of HBPA$^8$-SP was first studied using a C-terminal directed antibody to SP (Too et al., 1989) to confirm the identities of the D- and L-diastereomers. A displacement curve for [$^{125}$I] BHSP by HBPA$^8$-SP was determined by radioimmunoassay using this SP antibody (FIG. 5). The IC$_{50}$ for HBPA$^8$-SP HPLC peak 1 was 52±8 pM and for HPLC peak 2 was 390±40 pM, as compared to that for SP at 71±6 pM. Thus, peak 1 was confirmed to be the L-HBPA$^8$-SP diastereomer and peak 2 the D-HBPA$^8$-SP diastereomer, which is consistent with the HPLC results. Marfey's reagent (Marfey, P., Carlsberg Res. Commun. 49, 591–596 (1984)) has also been used to determine the absolute identity of the diastereomers (Blanton et al., 1994).

Binding studies of the peptide analog with SPR in P388D$_1$ cells confirmed that the photoprobe was a high affinity ligand for SPR as well as the identity of the D- and L-diastereomers. [$^{125}$I]-L-HBPA$^8$-SP bound to SPR was displaced by SP and displayed a typical high affinity binding curve for SPR in P388D$_1$ cells (FIG. 6). The IC$_{50}$ for SP displacement of [$^{125}$I]-L-HBPA$^8$-SP was determined by non-linear least squares analysis to be 0.11±0.01 nM from four independent experiments, whereas the IC$_{50}$ for D-HBPA$^8$-SP displacement of [$^{125}$I]BHSP was 1.50 nm±0.34 nM; the IC$_{50}$ for SP displacement of [$^{125}$I]BHSP was found to be 0.28±0.07 nM. Further binding studies (not shown) with these ligands and others are also consistent with the conclusion that L-HBPA$^8$-SP and [$^{125}$I]HBPA$^8$-SP, like L-BPA$^8$-SP (Li et al., 1995a), bind with high affinity and specificity to SPR. Results with HBPA substituted in position 3 of the SP peptide also demonstrates high affinity for SPR (not shown).

Photoaffinity Labeling of SP Receptor—Prior to synthesis of HBPA, to address concerns about the possible loss of radioiodine from the new photophore during photolysis, [$^{125}$I]-3-iodo-4-hydroxybenzophenone was prepared from 4-hydroxybenzophenone by standard oxidative radioiodination. The molecule was then subjected to photolysis under conditions identical to those used for receptor photolabeling with [$^{125}$I]BPA-SP (Li et al., 1995a), but using twice the photolysis time. After photolysis, greater than 98% of the radioiodine remained incorporated in the starting material. Using these same conditions, which gave efficient crosslinking using BPA$^8$-SP, only modest photolabeling of SPR by [$^{125}$I]HBPA$^8$-SP was observed. Thus, it was desirable to modify the photolysis conditions to increase the efficiency of photolabeling SPR in P388D$_1$ cells with [$^{125}$I]HBPA$^8$-SP. Increasing the time of photolysis increased the incorporation of [$^{125}$I]HBPA$^8$-SP only negligibly (from <1% at 15 min to 2.8% incorporation at 2 h). Freezing the sample prior to and during photolysis resulted in a significant increase in incorporation (to 2.9% for 15 min and 30% for 2 h photolyses). A major broad band (approximately 98% of total counts) at approximately 50–75 kDa was apparent on SDS-PAGE after photoinsertion of [$^{125}$I]HBPA$^8$-SP in P388D$_1$ cells, with a minor band of the unincorporated [$^{125}$I]-HBPA$^8$-SP at the gel front. The broad band is a result of the heterogeneous glycosylation of SP receptor (Li et al., 1995a; Vigna, S. R., Bowden, J. J., McDonald, D. M., Fisher, J., Okamoto, A., McVey, D. C., Payan, D. G. and Bunnett, N. W., J. Neurosci. 14, 834–845 (1994)). The photolabeling was completely inhibited by the presence of excess unlabeled SP or a specific nonpeptide SPR antagonist CP-96,345 in parallel experiments, showing specificity. No incorporation of the peptide was observed upon incubation of cells with [$^{125}$I] HBPA$^8$-SP in the dark. Experiments performed with [$^{125}$I] HBPA$^3$-SP gave similar results but with lower levels of incorporation.

DISCUSSION

Figure 3C:
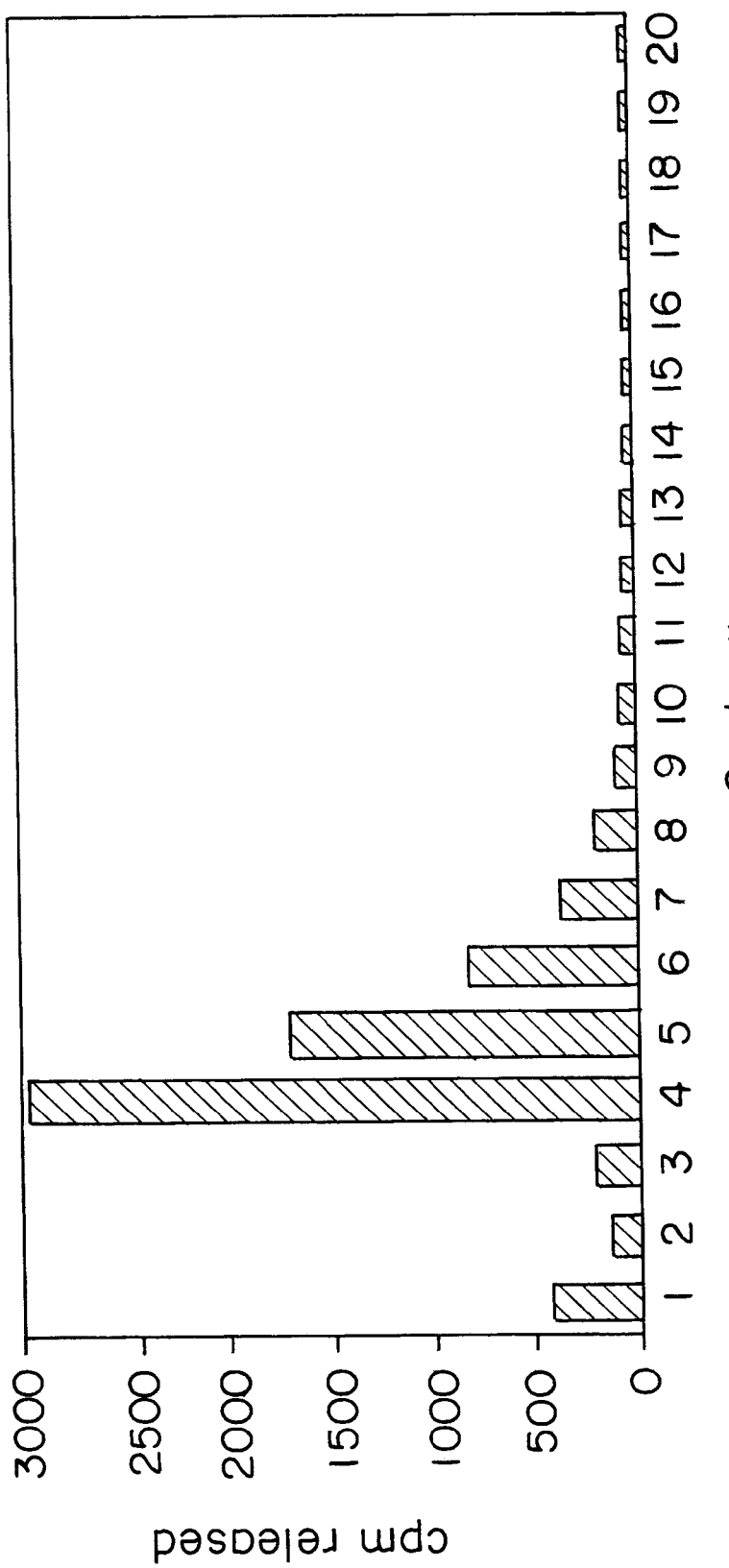
FIG. 3c is a histogram showing sequence analysis of an BSA•HBPA$^3$-SP peptide. The counts from the purified peptide fragment containing the BSA•HBPA$^3$-SP adduct are released in cycle 4 defining the photoinsertion site of [$^{125}$I] HBPA$^3$-SP into BSA. This release demonstrates that a PTH-HBPA•amino acid derivative can be released using standard Edman sequencing conditions.
Figure 4:
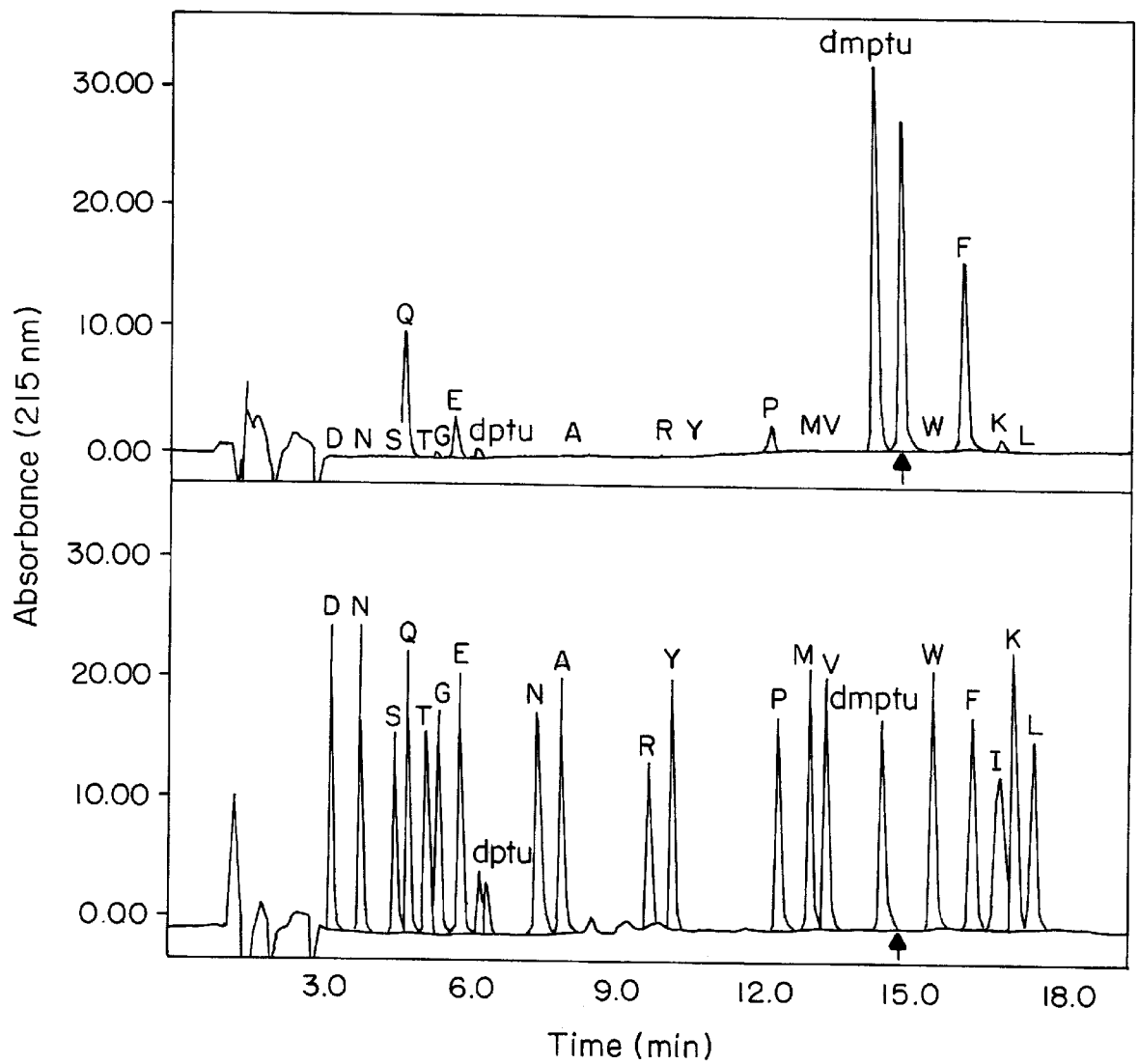
FIG. 4 is a chromatogram showing the elution pattern from sequencer for PTH•HBPA. The PTH derivative of HBPA elutes at 15.3 min in a standard Edman degradation sequencing run as shown by the arrow in this cycle (#8; top panel) of the sequencing of HBPA$^8$-SP. This position does not overlap with any other amino acids as seen in the PTH standards (bottom panel), allowing easy detection of the analog. In contrast, PTH-BPA is not detectable. PTH-amino acids are indicated using standard one-letter abbreviations; dptu and dmptu are typical side products of Edman sequencing.

Described herein is the synthesis of a benzophenone-based photoactivatable amino acid (HBPA) that can be incorporated into peptides by solid-phase synthesis and subsequently radiolabeled to quantitative specific activity with $^{125}$I. The ability to radioiodinate the photoreactive residue of a peptide ligand provides a distinct advantage over previous photo,labeling methods by allowing the identification of the exact amino acid at the photoinsertion site on the receptor as opposed to the mere identification of a fragment or region of the receptor. The strategy of putting $^{125}$I within a photoreactive moiety was introduced by Ruoho and coworkers (Lownder, J. M., Hokin-Neaverson, M. and Ruoho, A. E., Anal. Biochem. 168, 39–47 (1988); Morris, D. I., Robbins, J. D., Ruoho, A. E., Sutkowski, E. M. and Seamon, K. B., *J. Biol. Chem.* 266, 13377–13384 (1991)) for iodoazidophenyl derivatives. HBPA adds to this concept the significant advantages of a photolabile amino acid which can be placed anywhere in a peptide ligand during synthesis and the significant advantage of benzophenone photochemistry, providing an excellent tool for mapping binding sites. The specific interactions between each residue of the peptide ligand and the binding-site amino acids of the receptor can thus be identified by replacing each amino acid of the peptide. Additionally, unlike BPA, HBPA is easily identified using standard peptide sequencing methodology (FIG. 4), providing the options of detection by standard sequencing technology or radioisotope tracking of the mapping process. This resolution of HBPA (but not BPA) in the sequencing cycle is most likely due to the differences in polarity between HBPA and BPA. The retention of the $^{125}$I through sequencing and release (FIG. 3c) until the photo-insertion site is identified is extremely advantageous, especially in systems where receptor quantity is very limited. The adduct of the photolabel and the photo inserted amino acid after crosslinking and enzymatic digestion is observed by Edman degradation as detected by count release of the PTH derivative (FIG. 3c).

Benzoylphenylalanine-containing analogs of SP efficiently label the NK-1 receptor (Li et al., 1995a; Boyd, N. D., Macdonald, S. G., Kage, R., Luber-Narod, J. and Leeman, S. E., *Ann. New York Acad. Sci.* 632, 79–93 (1991a); Boyd, N. D., White, C. F., Cerpa, R, Kaiser, E. T. and Leeman, S. E., *Biochemistry* 30, 336–342 (1991b); Boyd, N. D., Kage, R. K. and Leeman, S. E., *The Tachykinin Receptors* (Buck, S. H., ed) pp. 219–236, Humana Press, Totowa, N.J. (1994); Boyd, N. D., Kage, R. K., Dumas, J. J., Krause, J. E. and Leeman, S. E., *Proc. Natl. Acad. Sci. USA* 93, 433–437 (1996); Kage, R. K., Leeman, S. E. and Boyd, N. D., *J. Neurochem.* 60, 347–351 (1993)) and were successful in identifying the regions of insertion of SP into SP receptor (Li et al., 1995a; Boyd et al., 1996). Agonist-binding domains of the receptor, directly identified by photoaffinity labeling (Li et al., 1995a), did not match those identified as; necessary for binding by mutagenesis (Huang et al., 1994a), demonstrating the importance of the photo-labeling technique by providing novel information that was complementary to that provided from mutagenesis. A BPA analog of SP has also been employed to identify the region of the nicotinic acetylcholine receptor which interacts with SP (Blanton et al., 1994).

In the first use of BPA for peptide photoaffinity labeling (Kauer et al., 1986), an optically pure peptide ligand was produced by chemical acetylation and enzymatic deacetylation prior to peptide synthesis to resolve L-BPA from D-BPA. Our subsequent work (Li et al., 1995a; Blanton et al., 1994) showed that this step is unnecessary in the case of substance P, as the racemic BPA can be used directly in peptide synthesis and the resulting diastereomeric peptides resolved by RP-HPLC during peptide purification. This result and work by others (Williams and Shoelson, 1993; Shoelson, S. E., Lee, J., Lynch, C. S., Backer, J. M., & Pilch, P. F., *J. Biol. Chem.* 268, 4085–4091 (1993); Miller and Kaiser, 1988) incorporating BPA into other peptides suggests that the resolution of racemic BPA prior to peptide synthesis is generally unnecessary, allowing the more efficient approach of omitting the yield-reducing and somewhat cumbersome steps required to resolve the amino acid. With HBPA, as with BPA (Li et al., 1995a; Blanton et al., 1994; Williams and Shoelson, 1993; Shoelson et al., 1993; Miller and Kaiser, 1988), resolution of the amino acid prior to solid phase peptide synthesis of the photolabile SP peptide analog is not required, and resolution of the optically pure peptides is instead carried out by RP-HPLC after its synthesis (FIG. 2).

The photoreactive analog of SP was easily radiolabeled to the high specific activity (2000 Ci/mmol) required for studies of peptide receptors by oxidative iodination of the HBPA residue at position 8 (or 3) with Na$^{125}$I using established methods. Concern that the bulkiness of the HBPA sidechain, before or after iodination, might result in a ligand of lower affinity proved unfounded, as the affinity of L-HBPA$^8$-SP and [$^{125}$I]-L-HBPA$^8$-SP for the murine SP receptor was similar to that of native SP (FIG. 6). Additionally, the affinity of L-HBPA$^8$-SP and [$^{125}$I]-L-HBPA$^8$-SP for anti-SP antiserum was similar to that of native SP. Both the antibody (Too et al., 1989) and SPR (Maggio, J. E. and Mantyh, P. W., *The Tachykinin Receptors* (Buck, S. H., ed) pp. 1–21, Humana Press, Totowa, N.J. (1994)) recognize the C-terminal 5 amino acids of SP (—PhePheGlyLeuMet-NH$_2$) . Both antiserum (FIG. 5) and receptor (FIG. 6) demonstrated the expected significant preference of L- over D-stereochemistry. Displacement studies (FIGS. 6) with unlabeled SP and a nonpeptide antagonist of NK-1/SP receptor demonstrated that L-HBPA$^8$-SP, like L-BPA$^8$-SP (Li et al., 1995a), is a specific as well as a high affinity ligand for the receptor. Although the bulkiness of HBPA is well tolerated in several positions in SP, tolerance of substitutions in the general case is both position and ligand/receptor specific. There are positions in some peptides which may not accept the bulk of this amino acid derivative, presenting a limitation to the photoscanning method described above (or any such method).

Concern that [$^{125}$I]-L-HBPA$^8$-SP might lose radioiodine during receptor photolabeling and subsequent workup or react to photolysis very differently than L-BPA$^8$-SP also proved unfounded, as covalent incorporation of $^{125}$I into SP receptor proceeded with high efficiency. Quantitation of the $^{125}$I and sequencing of the radiolabeled HBPA-SP peptides before and after photolysis showed little loss of $^{125}$I. Further support for the photochemical stability of the radioiodine in the hydroxybenzoyl ring was shown by Koch, T., Suenson, E. Korsholm, B., Henriksen, U. and Buchardt, O., *Bioconjugate Chem.* 5, 205–212 (1994).

The potential utility for HBPA is underscored by the wide range of peptide receptors that have been the target of photoaffinity labeling with BPA (Adams et al., 1995; Behar et al., 1996; Blanton et al., 1994; Bosse et al., 1993; Boyd et al., 1991a,b, 1994, 1996; Gao et al., 1995; Garcia et al., 1994; Gergel et al., 1994; Hampe, W., Frank, R. W., Schulze, C., Dehning, I. and Schaller, H. C., *Eur. J. Biochem.* 235, 814–820 (1996); Kage et al., 1993; Kauer et al., 1986; Keutmann, H. T. and Rubin, D. A., *Endocrinology* 132, 1305–1312 (1993); Li et al., 1995a; Macdonald et al., 1996; McNicoll et al., 1992; Miller and Kaiser, 1988; Nakamoto, C., Behar, V., Chin, K. R., Adams, A. E., Suva, L. J., Rosenblatt, M. and Chorev, M., *Biochemistry* 34, 10546–10552 (1995); O'Neil et al., 1989; Servant et al., 1993; Shoelson et al., 1993; Yamada, M., Kuliopulos, A., Nelson, N. P., Roth, D. A., Furie, B., Furie, B. C. and Walsh, C. T., *Biochemistry* 34, 481–489, (1995); Zhang et al., 1996; the teachings of these references are incorporated herein by reference). This novel amino acid may allow the exact site(s) of interaction(s) between peptide and protein receptors of low abundance to be identified in many systems. Its high insertion yield (about 30% in the present example) is especially useful for systems like the neuropeptide substance P which have very low levels of receptor available for study. Although Stull and coworkers (Gao et al., 1995) have identified specific sites of interaction between a [³H]-acetyl-BPA peptide substrate and myosin light chain kinase, this was only possible because BPA was the N-terminal amino acid of the substrate and the target protein was soluble and abundantly available from an overexpressed system. In contrast, HBPA may allow identification of insertion sites on rare proteins with the photolabile amino acid located at any position within the photoligand. Other systems which have significantly lower affinities (i.e., the interaction of SP with an allosteric site on the nicotinic acetylcholine receptor, Blanton et al., 1994) will also find this analog useful in mapping the specific binding site by retaining the advantageous properties associated with BPA (high photoinsertion efficiency, inertness to water) but adding the ability to incorporate a high specific activity label into the photoreactive residue.

The synthesis of HBPA opens a new era in studying peptide receptor interactions by allowing the concept of photoaffinity scanning to be more fully realized. It is the first amino acid that may allow the identification of specific interactions between a receptor of low abundance and a specific residue of its peptide ligand because the photoreactive residue can be radioiodinated while retaining the advantages of benzophenone photochemistry. By synthesis of a series of peptides for crosslinking, it will facilitate construction of a detailed interaction map of peptide receptors and their ligands. The peptides used here, HBPA-containing analogs of SP, bind with approximately the same potency and pharmacological specificity as the native agonist. The ligands are radioiodinatable after solid phase synthesis, crosslink with high efficiency, and the specific photoinsertion site in the primary sequence of the receptor may be identifiable because the radiolabel does not have to be placed at a site distal to the photoreactive moiety. The novel amino acid, HBPA, can be synthesized in bulk, incorporated into peptides in any position using standard Fmoc chemistry, radioiodinated, photocrosslinked, and released as a PTH derivative. These properties significantly enhance the ability to detect specific insertion sites of peptide ligands into receptors of low abundance.

ABBREVIATIONS

The abbreviations used are: BHSP, Bolton-Hunter substance P; BPA, 4-benzoyl-phenylalanine; BSA, bovine serum albumin; CIMS, chemical ionization mass spectrometry; CP-96,345, (2S, 3S)-cis-2-(diphenylmethyl)-N-[(2-methoxyphenyl)-methyl]- 1-aza-bicyclo[2.2.2]octan-3-amine; DMEM, Dulbecco's Modified Eagle's Medium; dmptu, dimethylphenylthiourea; dptu, diphenylthiourea; ESIMS, electrospray ionization mass spectrometry; FBS, fetal bovine serum; Fmoc, fluoren-9-yl-methoxycarbonyl; Fmoc-OSu, fluoren-9-ylmethoxycarbonyl N-hydroxy-succinimide ester; HBPA, p-(4-hydroxybenzoyl)-phenylalanine; MALDMS, matrix-assisted laser desorption mass spectrometry; NK-1R, neurokinin-1 receptor (also known as substance P receptor); NMR, nuclear magnetic resonance; PAGE, polyacrylamide gel electrophoresis; PTH, phenylthiohydantoin; $R_f$, relative mobility; RIA, radioimmunoassay; RP-HPLC, reverse phase high performance liquid chromatography; SP, substance P; SPR, substance P receptor; TFA, trifluoroacetic acid; TLC, thin layer chromatography; UV, ultraviolet.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed:

1. A compound represented by the following structural formula:

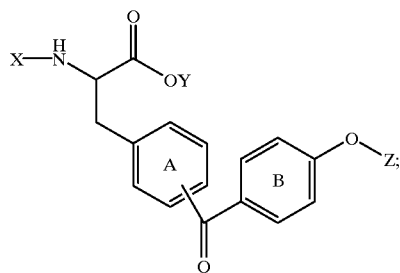

wherein:

Phenyl Ring A and Phenyl Ring B are independently substituted or unsubstituted;

X is —H or an amine protecting group;

—OY is —OH, an activating group for a carboxylic acid or a protecting group for a carboxylic acid; and Z is —H or a phenolic protecting group, with the proviso that Z is not a straight chained, saturated alkyl group and at least one of X, Y or Z is not —H.

2. The compound of claim 1 wherein the compound is represented by the following structural formula:

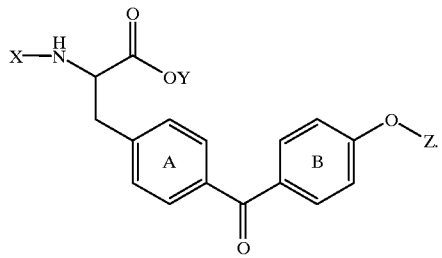

3. The compound of claim 2 wherein:

X is —H; and

—OY is a protecting group for a carboxylic acid.

4. The compound of claim 3 wherein Phenyl Ring A and Phenyl Ring B are each unsubstituted.

5. The compound of claim 3 wherein Phenyl Ring B is substituted ortho to the hydroxy group with tritium or $^{125}$I.

6. The compound of claim 5 wherein Phenyl Ring B is monosubstituted and Phenyl Ring A is unsubstituted.

7. The compound of claim 2 wherein:

X is an amine protecting group; and

Y is —H.

8. The compound of claim 7 wherein Phenyl Ring A and Phenyl Ring B are each unsubstituted.

9. The compound of claim 7 wherein Ring B is substituted ortho to the hydroxy group with tritium or $^{125}$I.

10. The compound of claim 9 wherein Phenyl Ring B is monosubstituted and Phenyl Ring A is unsubstituted.

11. A photoreactive polypeptide comprising at least one (p-hydroxybenzoyl) phenylalanyl group in the polypeptide chain, wherein the (p-hydroxybenzoyl) phenylalanyl group is represented by the following structural formula:

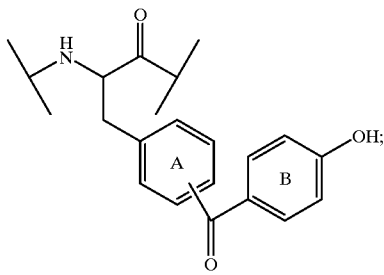

wherein Phenyl Ring A and Phenyl Ring B are independently substituted or unsubstituted.

12. The photoreactive polypeptide of claim 11 wherein the (p-hydroxylbenzoyl) phenylalanyl group is represented by the following structural formula:

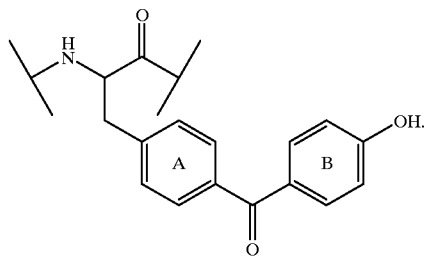

13. The photoreactive polypeptide of claim 12 wherein Phenyl Ring A and Phenyl Ring B are each unsubstituted.

14. The photoreactive polypeptide of claim 12 wherein Phenyl Ring B is substituted ortho to the hydroxy group with tritium or $^{125}$I.

15. The photoreactive polypeptide of claim 14 wherein Phenyl Ring B is monosubstituted and Phenyl Ring A is unsubstituted.

16. A method of forming a covalent bond between a target molecule and a photoreactive polypeptide which can form a complex with the target molecule, wherein the photoreactive polypeptide comprises in the polypeptide chain at least one (p-hydroxybenzoyl) phenylalanyl group represented by the following structural formula:

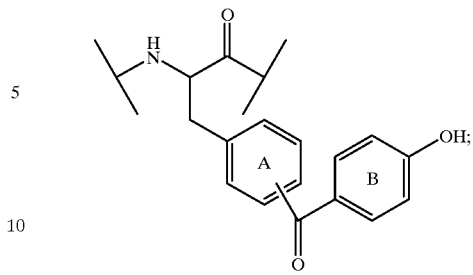

wherein Phenyl Ring A and Phenyl Ring B are independently substituted or unsubstituted;
said method comprising the steps of:
a) mixing the photoreactive polypeptide with the target molecule under conditions suitable for forming a complex between the photoreactive polypeptide and the target molecule; and
b) photolyzing the complex formed in step a) under conditions suitable for reacting the target molecule with the photoreactive polypeptide, thereby forming a covalent bond between the target molecule and the photoreactive polypeptide.

17. The method of claim 16 wherein the (p-hydroxybenzoyl) phenylalanyl group is represented by the following structural formula:

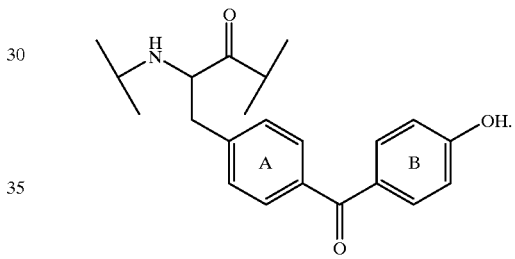

18. The method of claim 17 wherein Phenyl Ring A and Phenyl Ring B are each unsubstituted.

19. The method of claim 17 wherein Phenyl Ring B is substituted ortho to the hydroxy group with tritium or $^{125}$I.

20. The method of claim 19 wherein Phenyl Ring B is monosubstituted and Phenyl Ring A is unsubstituted.

21. The compound of claim 2 wherein:
X is Fmoc;
—OY is —OH; and
Z is —H.

* * * * *